(12) United States Patent
Moon et al.

(10) Patent No.: US 11,963,746 B2
(45) Date of Patent: *Apr. 23, 2024

(54) BODY-WORN VITAL SIGN MONITOR

(71) Applicant: SOTERA WIRELESS, INC., San Diego, CA (US)

(72) Inventors: Jim Moon, San Diego, CA (US); Henk Visser, II, San Diego, CA (US); Robert Kenneth Hunt, Vista, CA (US); Devin McCombie, Carlsbad, CA (US); Marshal Singh Dhillon, San Diego, CA (US); Matthew J. Banet, San Diego, CA (US)

(73) Assignee: SOTERA WIRELESS, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/409,465

(22) Filed: Aug. 23, 2021

(65) Prior Publication Data

US 2022/0248961 A1    Aug. 11, 2022

Related U.S. Application Data

(63) Continuation of application No. 16/504,798, filed on Jul. 8, 2019, now Pat. No. 11,096,596, which is a (Continued)

(51) Int. Cl.
*A61B 5/021* (2006.01)
*A61B 5/0205* (2006.01)
(Continued)

(52) U.S. Cl.
CPC .......... *A61B 5/021* (2013.01); *A61B 5/02125* (2013.01); *A61B 5/318* (2021.01);
(Continued)

(58) Field of Classification Search
CPC ........ A61B 5/021–0235; A61B 5/0402; A61B 5/02125; A61B 2560/0223; A61B 5/0205;
(Continued)

(56) References Cited

U.S. PATENT DOCUMENTS 4,086,916 A    5/1978    Freeman et al.
4,263,918 A    4/1981    Swearingen et al.
(Continued)

FOREIGN PATENT DOCUMENTS

EP    0443267 A1    8/1991
EP    0993803 A1    4/2000
(Continued)

OTHER PUBLICATIONS

Soh et al., An investigation of respiration while wearing back belts. Applied Ergonomics 1997; 28(3):189-192.
(Continued)

*Primary Examiner* — Brian T Gedeon
(74) *Attorney, Agent, or Firm* — Acuity Law Group, PC; Michael A. Whittaker

(57) ABSTRACT

The invention provides a body-worn monitor featuring a processing system that receives a digital data stream from an ECG system. A cable houses the ECG system at one terminal end, and plugs into the processing system, which is worn on the patient's wrist like a conventional wristwatch. The ECG system features: i) a connecting portion connected to multiple electrodes worn by the patient; ii) a differential amplifier that receives electrical signals from each electrode and process them to generate an analog ECG waveform; iii) an analog-to-digital converter that converts the analog ECG waveform into a digital ECG waveform; and iv) a transceiver that transmits a digital data stream representing the digital ECG waveform (or information calculated from the waveform) through the cable and to the processing system.

(Continued)

Different ECG systems, typically featuring three, five, or twelve electrodes, can be interchanged with one another.

1 Claim, 17 Drawing Sheets

Related U.S. Application Data continuation of application No. 15/717,645, filed on Sep. 27, 2017, now Pat. No. 10,342,438, which is a continuation of application No. 12/560,104, filed on Sep. 15, 2009, now abandoned.

(51) Int. Cl.
*A61B 5/08* (2006.01)
*A61B 5/1455* (2006.01)
*A61B 5/318* (2021.01)
*H04L 1/00* (2006.01)
*A61B 5/369* (2021.01)

(52) U.S. Cl.
CPC ............ *A61B 5/0205* (2013.01); *A61B 5/08* (2013.01); *A61B 5/14551* (2013.01); *A61B 5/369* (2021.01); *A61B 2560/0223* (2013.01); *A61B 2562/0219* (2013.01); *H04L 1/0078* (2013.01); *H04L 1/0083* (2013.01)

(58) Field of Classification Search
CPC ..... A61B 5/0476; A61B 5/08; A61B 5/14551; A61B 2562/0219; H04L 1/0078; H04L 1/0083
See application file for complete search history.

(56) References Cited

U.S. PATENT DOCUMENTS

| | | |
|---|---|---|
| 4,270,547 A | 6/1981 | Steffen et al. |
| 4,305,400 A | 12/1981 | Logan |
| 4,367,752 A | 1/1983 | Jimenez et al. |
| 4,577,639 A | 3/1986 | Simon et al. |
| 4,582,068 A | 4/1986 | Phillipps et al. |
| 4,653,498 A | 3/1987 | New, Jr. et al. |
| 4,710,164 A | 12/1987 | Levin et al. |
| 4,722,351 A | 2/1988 | Phillipps et al. |
| 4,802,486 A | 2/1989 | Goodman et al. |
| 4,807,638 A | 2/1989 | Sramek |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,224,928 A | 7/1993 | Sibalis et al. |
| 5,247,931 A | 9/1993 | Norwood |
| 5,289,824 A | 3/1994 | Mills et al. |
| 5,316,008 A | 5/1994 | Suga et al. |
| 5,339,818 A | 8/1994 | Baker et al. |
| 5,348,008 A | 9/1994 | Bornn et al. |
| 5,435,315 A | 7/1995 | McPhee et al. |
| 5,448,991 A | 9/1995 | Polson et al. |
| 5,465,082 A | 11/1995 | Chaco |
| 5,469,150 A | 11/1995 | Sitte |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,568,814 A | 10/1996 | Gallant et al. |
| 5,575,284 A | 11/1996 | Athan et al. |
| 5,577,508 A | 11/1996 | Medero |
| 5,588,427 A | 12/1996 | Tien |
| 5,593,431 A | 1/1997 | Sheldon |
| 5,632,272 A | 5/1997 | Diab et al. |
| 5,645,060 A | 7/1997 | Yorkey |
| 5,649,543 A | 7/1997 | Hosaka et al. |
| 5,680,870 A | 10/1997 | Hood et al. |
| 5,685,299 A | 11/1997 | Diab et al. |
| 5,701,894 A | 12/1997 | Cherry et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | Delorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lichter et al. |
| 6,160,478 A | 12/2000 | Jacobsen et al. |
| 6,168,569 B1 | 1/2001 | McEwen et al. |
| 6,176,831 B1 | 1/2001 | Voss et al. |
| 6,198,394 B1 | 3/2001 | Jacobsen et al. |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 | 7/2001 | Anderson et al. |
| 6,263,222 B1 | 7/2001 | Diab et al. |
| 6,287,262 B1 | 9/2001 | Amano et al. |
| 6,322,516 B1 | 11/2001 | Masuda et al. |
| 6,334,065 B1 | 12/2001 | Al-Ali et al. |
| 6,371,921 B1 | 4/2002 | Caro et al. |
| 6,388,240 B2 | 5/2002 | Schulz et al. |
| 6,416,471 B1 | 7/2002 | Kumar et al. |
| RE37,852 E | 9/2002 | Aso et al. |
| 6,443,890 B1 | 9/2002 | Schulze et al. |
| 6,480,729 B2 | 11/2002 | Schulz et al. |
| 6,491,647 B1 | 12/2002 | Bridger et al. |
| 6,503,206 B1 | 1/2003 | Li et al. |
| 6,514,218 B2 | 2/2003 | Yamamoto |
| 6,516,289 B2 | 2/2003 | David |
| 6,526,310 B1 | 2/2003 | Carter et al. |
| 6,527,729 B1 | 3/2003 | Turcott |
| 6,533,729 B1 | 3/2003 | Khair et al. |
| 6,541,756 B2 | 4/2003 | Schulz et al. |
| 6,544,173 B2 | 4/2003 | West et al. |
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,605,038 B1 | 8/2003 | Teller et al. |
| 6,606,993 B1 | 8/2003 | Wiesmann et al. |

(56) References Cited

U.S. PATENT DOCUMENTS

| | | |
|---|---|---|
| 6,616,606 B1 | 9/2003 | Petersen et al. |
| 6,645,154 B2 | 11/2003 | Oka |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 | 9/2004 | Mault et al. |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,912,414 B2 | 6/2005 | Tong |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,004,907 B2 | 2/2006 | Banet et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,079,888 B2 | 7/2006 | Oung et al. |
| 7,115,824 B2 | 10/2006 | Lo |
| 7,156,809 B2 | 1/2007 | Quy |
| 7,179,228 B2 | 2/2007 | Banet |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,237,446 B2 | 7/2007 | Chan et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | DeLonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,925,022 B2 | 4/2011 | Jung et al. |
| 7,976,480 B2 | 7/2011 | Grajales et al. |
| 7,983,933 B2 | 7/2011 | Karkanias et al. |
| 7,993,275 B2 | 8/2011 | Banet et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 8,364,250 B2 | 1/2013 | Moon et al. |
| 8,419,649 B2 | 4/2013 | Banet et al. |
| 8,449,469 B2 | 5/2013 | Banet et al. |
| 8,527,038 B2 | 9/2013 | Moon et al. |
| 8,574,161 B2 | 11/2013 | Banet et al. |
| 9,149,192 B2 | 10/2015 | Banet et al. |
| 10,342,438 B2 | 7/2019 | Moon et al. |
| 11,096,596 B2 | 8/2021 | Moon et al. |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0158775 A1 | 10/2002 | Wallace |
| 2002/0170193 A1 | 11/2002 | Townsend et al. |
| 2002/0183627 A1 | 12/2002 | Nishii et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Conner et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |

(56) References Cited

U.S. PATENT DOCUMENTS

| | | |
|---|---|---|
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0119833 A1 | 6/2005 | Nanikashvili |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0216199 A1 | 9/2005 | Banet |
| 2005/0228296 A1 | 10/2005 | Banet |
| 2005/0228297 A1 | 10/2005 | Banet et al. |
| 2005/0228298 A1 | 10/2005 | Banet et al. |
| 2005/0228299 A1 | 10/2005 | Banet |
| 2005/0228300 A1 | 10/2005 | Jaime et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0261598 A1 | 11/2005 | Banet et al. |
| 2005/0265267 A1 | 12/2005 | Hwang |
| 2005/0283088 A1 | 12/2005 | Bernstein |
| 2006/0009697 A1* | 1/2006 | Banet ............... A61B 5/021 128/903 |
| 2006/0009698 A1 | 1/2006 | Banet et al. |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0084878 A1 | 4/2006 | Banet et al. |
| 2006/0122469 A1 | 6/2006 | Martel |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0208262 A1 | 9/2007 | Kovacs |
| 2007/0225609 A1 | 9/2007 | Rosch et al. |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |
| 2008/0039731 A1 | 2/2008 | McCombie et al. |
| 2008/0077026 A1 | 3/2008 | Banet et al. |
| 2008/0077027 A1 | 3/2008 | Allgeyer |
| 2008/0082001 A1 | 4/2008 | Hatlestad et al. |
| 2008/0082004 A1 | 4/2008 | Banet et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | LeBoeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112072 A1 | 4/2009 | Banet et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2009/0326349 A1 | 12/2009 | Mcgonigle et al. |
| 2010/0010380 A1 | 1/2010 | Panken et al. |
| 2010/0030034 A1 | 3/2010 | Schulhauser et al. |
| 2010/0030085 A1 | 3/2010 | Rojas Ojeda et al. |
| 2010/0056881 A1 | 3/2010 | Libbus et al. |
| 2010/0056886 A1 | 3/2010 | Hurtubise et al. |

(56) References Cited

U.S. PATENT DOCUMENTS

| | | |
|---|---|---|
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | Mccombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | Mccombie et al. |
| 2010/0298653 A1 | 11/2010 | Mccombie et al. |
| 2010/0298654 A1 | 11/2010 | Mccombie et al. |
| 2010/0298655 A1 | 11/2010 | Mccombie et al. |
| 2010/0298656 A1 | 11/2010 | Mccombie et al. |
| 2010/0298657 A1 | 11/2010 | Mccombie et al. |
| 2010/0298658 A1 | 11/2010 | Mccombie et al. |
| 2010/0298659 A1 | 11/2010 | Mccombie et al. |
| 2010/0298660 A1 | 11/2010 | Mccombie et al. |
| 2010/0298661 A1 | 11/2010 | Mccombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |
| 2018/0317826 A1 | 11/2018 | Muhsin et al. |

FOREIGN PATENT DOCUMENTS

| | | |
|---|---|---|
| EP | 2470067 A1 | 7/2012 |
| EP | 2544584 A1 | 1/2013 |
| GB | 2329250 A | 3/1999 |
| WO | 9932030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008110788 A1 | 9/2008 |
| WO | 2009009761 A1 | 1/2009 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Subbe et al., Effect of introducing the Modified Early Warning score on clinical outcomes, cardiopulmonary arrests and intensive care utilization in acute medical admissions. Anaesthesia Aug. 2003;58(8):797-802.

Talkowski, Quantifying Physical Activity in Community Dwelling Older Adults Using Accelerometry. University of Pittsburgh (Dissertation) 2008:1-91.

Thongpithoonrat et al., Networking and Plug-and-Play of Bedside Medical Instruments. Conf Proc IEEE Eng Med Biol Soc. 2008;2008:1514-1517.

Universal Serial Bus Specification. Revision 2.0. Apr. 27, 2000. 650 pgs.

USB 2.0 Specification Engineering Change Notice. Oct. 20, 2000 (45 pages).

Vuorela et al., Two portable long-term measurement devices for ECG and bioimpedance. Second International Conference on Pervasive Computing Technologies for Healthcare. Jan. 30-Feb. 1, 2008:169-172.

Weinhold et al., Buprenorphine alone and in combination with naloxone in non-dependent humans. Drug Alcohol Depend. Aug. 1992;30(3 ):263-274.

Wolf et al., Development of a Fall Detector and Classifier based on a Triaxial Accelerometer Demo Board. 2007:210-213.

Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College, Cambridge, UK, Aug. 19-22, 2007 (pp. 22-25).

Yang et al., Research on Multi-Parameter Physiological Monitor Based on CAN Bus. IFMBE Proceed. 2008; 19:417-419.

Zeltwanger, Controller Area Network and CANopen in Medical Equipment. Bus Briefing: Med Dev Manuf Technol. 2002:34-37.

Zislin et al., Ways of Improving the Accuracy of Arterial Pressure Oscillometry. Biomedical Engineering 2005;39(4):174-178.

Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.

International Search Report and Written Opinion dated Jul. 22, 2011 issued in PCT/US2011/027843 (36 pages).

International Preliminary Report on Patentability dated Sep. 11, 2012 issued in PCT/US2011/027843 (32 pages).

International Search Report and Written Opinion dated Nov. 5, 2010 issued in PCT/US2010/048866 (10 pages).

International Preliminary Report on Patentability dated Mar. 20, 2012 issued in PCT/US2010/048866 (9 pages).

(56) References Cited

OTHER PUBLICATIONS

Extended European Search Report and Written Opinion dated Aug. 29, 2013 issued in EP 10817733 (11 pages).
Extended European Search Report and Written Opinion dated Jun. 17, 2015 issued in EP 11754055 (15 pages).
Afonso et al., ECG Beat Detection Using Filter Banks. IEEE Trans Biomed Eng. Feb. 1999;46(2):192-202.
Ahlstrom et al., Noninvasive investigation of blood pressure changes using the pulse wave transit time: a novel approach in the monitoring of hemodialysis patients. J Artif Organs. 2005;8(3):192-197.
Allen et al., Classification of a known sequence of motions and postures from accelerometry data using adapted Gaussian mixture models. Physiol Meas. 2006;27:935-951.
Alves et al., CAN Protocol: A Laboratory Prototype for Fieldbus Applications. XIX IMEKO World Congress Fundamental and Applied Metrology Sep. 6-11, 2009, Lisbon, Portugal. 4 pp. 454-457 ISBN 978-963-88410-0-1.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Benefits of Digital Sensors. Gems Sensors. Feb. 14, 2008. http://web.archive.org/web/20080214122230/http://www.sensorland.com/HowPage054.html.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Chan et al., Noninvasive and Cuffless Measurements of Blood Pressure For Telemedicine. Proceedings of the 23rd Annual International Conference of the IEEE Engineering in Medicine and Biology Society 2001:3 pages.
Clifford et al., Measuring Tilt with Low-g Accelerometers. Freescale Semiconductor, Inc., 2005:8 pages.
Cretikos et al., The Objective Medical Emergency Team Activation Criteria: a case-control study. Resuscitation Apr. 2007;73(1):62-72.
De Scalzi et al., Relationship Between Systolic Time Intervals and Arterial Blood Pressure. Clin Cardiol. 1986;9:545-549.
Drinnan et al., Relation between heart rate and pulse transit time during paced respiration. Physiol Meas. Aug. 2001;22(3):425-432.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993; 8(7):354-360.
Flash et al., The Coordination of Arm Movements: An Experimentally Confirmed Mathematical Model. J Neurosci. Jul. 1985;5(7):1688-1703.
Fung, Advisory System for Administration of Phenylephrine Following Spinal Anesthesia for Cesarean Section. Master's Thesis. University of British Columbia 2002: 119 pages.
Gallagher, Comparison of Radial and Femoral Arterial Blood Pressure in Children after Cardiopulmonary Bypass. J Clin Monit. Jul. 1985;1(3):168-171.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jackson, Digital Filter Design and Synthesis Using High-Level Modeling Tools. Virginia Polytechnic Institute and State University Thesis. Dec. 1999.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009 (14 pages).
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Kim et al., Two Algorithms for Detecting Respiratory Rate from ECG Signal. IFMBE Proceedings 2007;14(6)JC27:4069-4071.
Klabunde, Mean Arterial Pressure. Cardiovascular Physiology Concepts. Mar. 8, 2007.accessed online at: http://www.cvphysiology.com/Blood%20Pressure/BP006 (2 pages).
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.
Mason, Signal Processing Methods for Non-Invasive Respiration Monitoring. Department of Engineering Science, University of Oxford 2002 (175 pages).
Mathie et al., Classification of basic daily movements using a triaxial accelerometer. Med Biol Eng Comput. Sep. 2004;42(5):679-687.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
Mckneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor For Extreme Environments. Conf Proc IEEE Eng Med Biol Soc. 2004;3:2192-2195.
Nitzan et al., Effects of External Pressure on Arteries Distal to the Cuff During Sphygmomanometry. IEEE Transactions on Biomedical Engineering, Jun. 2005;52{6):1120-1127.
O'Haver, Peak Finding and Measurement, Version 1.6, Oct. 26, 2006. Accessed online at: https://terpconnect.umd.edu/~toh/spectrum/PeakFindingandMeasurement.htm (3 pages).
Otto et al., System Architecture of a Wireless Body Area Sensor Network for Ubiquitous Health Monitoring. Journal of Mobile Multimedia Jan. 10, 2006;1 (4):307-326.
Packet Definition. The Linux Information Project Jan. 8, 2006. Accessed online at: http://www.linfo.org/packet.html (2 pages).
Park et al., An improved algorithm for respiration signal extraction from electrocardiogram measured by conductive textile electrodes using instantaneous frequency estimation. Med Bio Eng Comput 2008;46:147-158.
Park et al., Direct Blood Pressure Measurements in Brachial and Femoral Arteries in Children. Circulation Feb. 1970;41(2):231-237.
PDF-Pro for iPhone & iPod touch User Manual. ePapyrus Jul. 2009;1:1-25 http://epapyrus.com/en/files/PDFPro%.
Poon and Zhang, Cuff-Less and Noninvasive Measurements of Arterial Blood Pressure by Pulse Transit Time. Conf Proc IEEE Eng Med Biol Soc. 2005;6:5877-5880.

(56) References Cited

OTHER PUBLICATIONS

Reddan et al., Intradialytic Blood Volume Monitoring in Ambulatory Hemodialysis Patients: A Randomized Trial. J Am Soc Nephrol. Jul. 2005;16(7):2162-2169.

Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.

RS-232. Wikipedia Dec. 5, 2008 Accessed online at: https://en.wikipedia.org/wiki/RS-232 (8 pages).

Scanaill et al., A Review of Approaches to Mobility Telemonitoring of the Elderly in Their Living Environment. Annals of Biomed Engineer. Apr. 2006;34(4):547-563.

Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.

Sifil et al., Evaluation of the Harmonized Alert Sensing Technology Device for Hemodynamic Monitoring in Chronic Hemodialysis Patients. ASAIO J. Nov.-Dec. 2003;49(6):667-672.

Signal Strength_ Oct. 6, 2008—Accessed online at: https://en.wikipedia.org/wiki/ Signal strength (3 pages).

\* cited by examiner

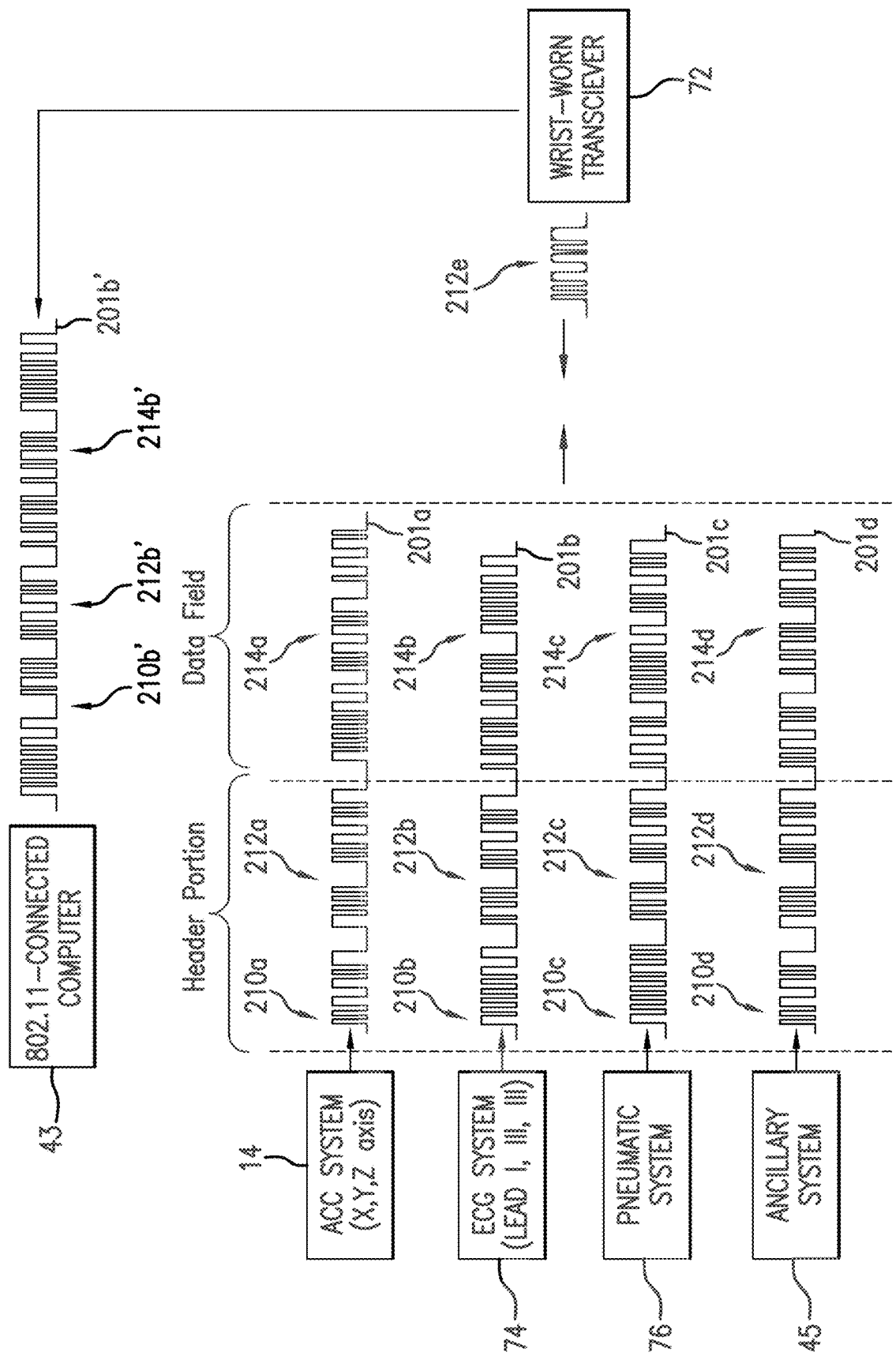

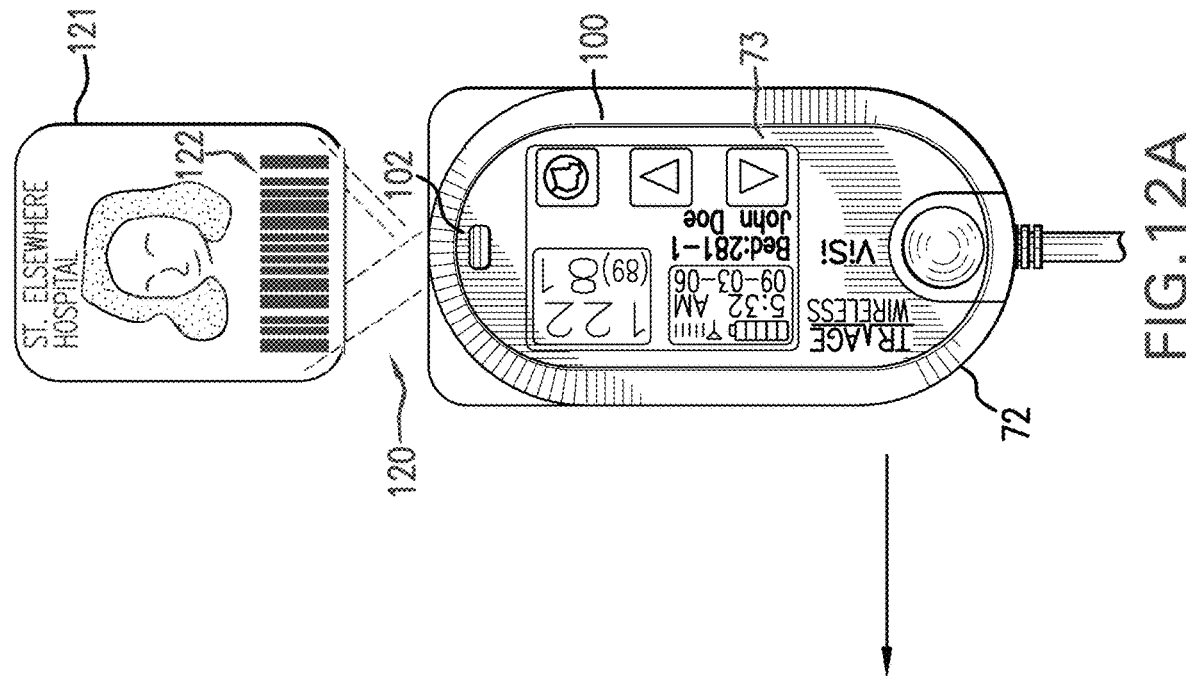
FIG. 12A
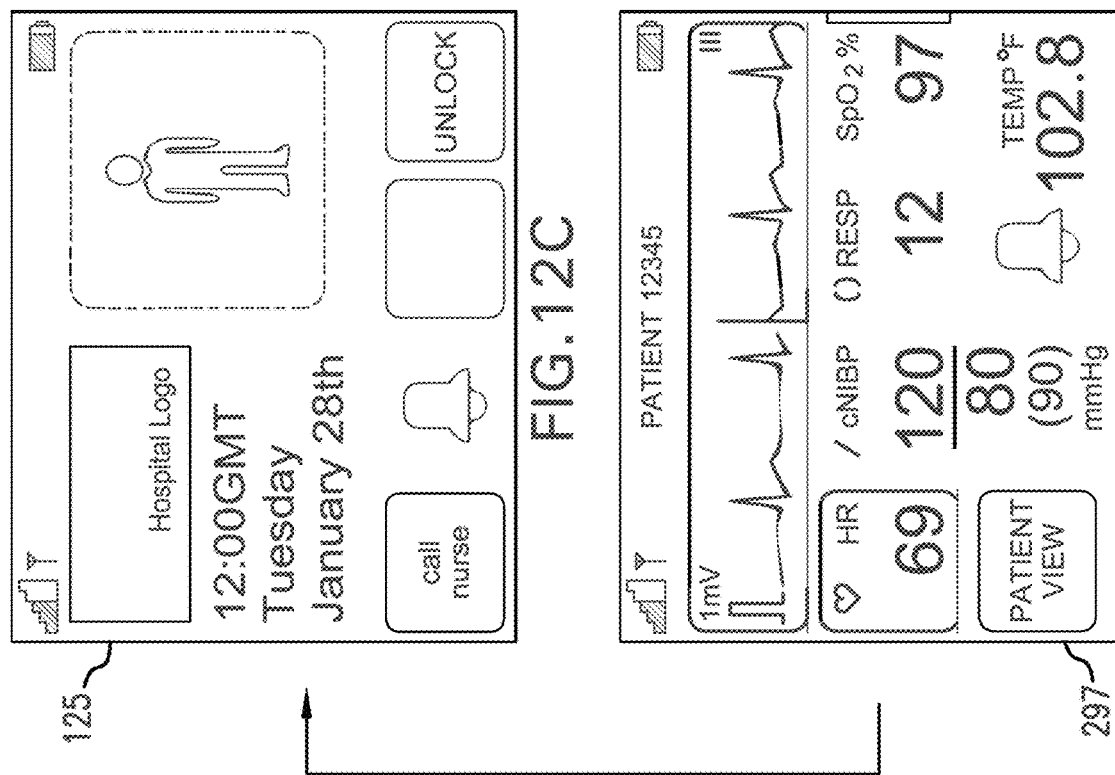
FIG. 12B
FIG. 12C

FIG. 15A

BODY-WORN VITAL SIGN MONITOR

CROSS REFERENCES TO RELATED APPLICATIONS

This application is a continuation application of U.S. patent application Ser. No. 16/504,798, filed Jul. 8, 2019, now U.S. Pat. No. 11,096,596, which is a continuation of U.S. patent application Ser. No. 15/717,645, filed Sep. 27, 2017, now U.S. Pat. No. 10,342,438, which is a continuation of U.S. patent application Ser. No. 12/560,104, filed Sep. 15, 2009, each of which is hereby incorporated in its entirety including all tables, figures and claims

BACKGROUND OF THE INVENTION

Field of the Invention

The present invention relates to medical devices for monitoring vital signs, e.g., arterial blood pressure.

Description of the Related Art

Conventional vital sign monitors are used throughout the hospital, and are particularly commonplace in high-acuity areas such as the intensive care unit (ICU), emergency department (ED), or operating room (OR). Patients in these areas are generally sick and require a relatively high degree of medical attention. The ratio between medical professionals and patient in these areas is typically high compared to lower-acuity areas of the hospital. Even in such areas, however, it is still common practice for medical professionals to measure vital signs such as blood pressure, respiratory rate, oxygen saturation (SpO2), heart rate, and temperature. Monitoring of these parameters is typically done with portable or wall-mounted vital sign monitors. It can be difficult to effectively monitor patients in this way, however, because they are often ambulatory and not constrained to a single hospital room. This poses a problem for conventional vital sign monitors, which are typically heavy and unwieldy, as they are not intended for the ambulatory population. Some companies have developed ambulatory vital sign monitors with limited capabilities (e.g. cuff-based blood pressure using oscillometry and SpO2 monitoring), but typically these devices only make intermittent, rather than continuous, measurements. And even these measurements tend to work best on stationary patients, as they are easily corrupted by motion-related artifacts.

Blood pressure is a vital sign often considered to be a good indicator of a patient's health. In critical care environments like the ICU and OR, blood pressure can be continuously monitored with an arterial catheter inserted in the patient's radial or femoral artery. Alternatively, blood pressure can be measured intermittently with a cuff using oscillometry, or manually by a medical professional using auscultation. Most vital sign monitors perform both the catheter and cuff-based measurements of blood pressure. Blood pressure can also be monitored continuously with a technique called pulse transit time (PTT), defined as the transit time for a pressure pulse launched by a heartbeat in a patient's arterial system. PTT has been shown in a number of studies to correlate to systolic (SYS), diastolic (DIA), and mean (MAP) blood pressures. In these studies, PTT is typically measured with a conventional vital signs monitor that includes separate modules to determine both an electrocardiogram (ECG) and SpO2. During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that clips to a patient's finger and includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation detected by the photodetector to determine the patient's blood oxygen saturation level and a time-dependent waveform called a photoplethysmograph (PPG). Time-dependent features of the PPG indicate both pulse rate and a volumetric absorbance change in an underlying artery caused by the propagating pressure pulse.

Typical PTT measurements determine the time separating a maximum point on the QRS complex (indicating the peak of ventricular depolarization) and a foot of the PPG waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff and oscillometry. Typically during the calibration process the blood pressure cuff is applied to the patient, used to make one or more blood pressure measurements, and then left for future measurements. Going forward, the calibration measurements are used, along with a change in PTT, to continuously measure the patient's blood pressure (defined herein as 'cNIBP'). PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and PPG, which are then processed to determine PTT. U.S. Pat. No. 5,964,701 describes a finger-ring sensor that includes an optical system for detecting a PPG, and an accelerometer for detecting motion.

SUMMARY OF THE INVENTION

To improve the safety of hospitalized patients, particularly those in lower-acuity areas, it is desirable to have a body-worn monitor that continuously measures a plurality of vital signs from a patient, and wirelessly transmits these directly to a nurse or to a central nursing station. Preferably the monitor operates algorithms featuring: 1) a low percentage of false positive alarms/alerts; and 2) a high percentage of true positive alarms/alerts. The term 'alarm/alert', as used herein, refers to an audio and/or visual alarm generated directly by a monitor worn on the patient's body, or alternatively a remote monitor (e.g., a central nursing station). To accomplish this, the invention provides a body-worn monitor that measures a patient's vital signs (e.g. blood pressure, SpO2, heart rate, respiratory rate, and temperature) while simultaneously characterizing their activity state (e.g. resting, walking, convulsing, falling) and posture (upright, supine). The body-worn monitor processes this information to minimize corruption of the vital signs and associated alarms/alerts by motion-related artifacts.

The body-worn monitor can include a software framework that generates alarms/alerts based on threshold values that are either preset or determined in real time. The framework additionally includes a series of 'heuristic' rules that take the patient's activity state and motion into account, and process the vital signs accordingly. These rules, for example, indicate that a walking patient is likely breathing and has a regular heart rate, even if their motion-corrupted vital signs suggest otherwise.

The body-worn monitor features a series of sensors that attach to the patient to measure time-dependent PPG, ECG, accelerometer-based motion (ACC), oscillometric (OSC), respiratory rate (RR), and impedance pneumography (IP) waveforms. A microprocessor (CPU) within the monitor continuously processes these waveforms to determine the patient's vital signs, degree of motion, posture and activity level. Sensors that measure these signals typically send digitized information to a wrist-worn transceiver through a serial interface, or bus, operating on a controlled area network (CAN) protocol. The CAN bus is typically used in the automotive industry, which allows different electronic systems to effectively and robustly communicate with each other with a small number of dropped packets, even in the presence of electrically noisy environments. This is particularly advantageous for ambulatory patients that may generate signals with large amounts of motion-induced noise.

Blood pressure, a vital sign that is particularly useful for characterizing a patient's condition, is typically calculated from a PTT value determined from the PPG and ECG waveforms. Once determined, blood pressure and other vital signs can be further processed, typically with a server within a hospital, to alert a medical professional if the patient begins to decompensate.

In other embodiments, PTT can be calculated from time-dependent waveforms other than the ECG and PPG, and then processed to determine blood pressure. In general, PTT can be calculated by measuring a temporal separation between features in two or more time-dependent waveforms measured from the human body. For example, PTT can be calculated from two separate PPGs measured by different optical sensors disposed on the patient's fingers, wrist, arm, chest, or virtually any other location where an optical signal can be measured using a transmission or reflection-mode optical configuration. In other embodiments, PTT can be calculated using at least one time-dependent waveform measured with an acoustic sensor, typically disposed on the patient's chest. Or it can be calculated using at least one time-dependent waveform measured using a pressure sensor, typically disposed on the patient's bicep, wrist, or finger. The pressure sensor can include, for example, a pressure transducer, piezoelectric sensor, actuator, polymer material, or inflatable cuff.

In one aspect, the invention provides a body-worn monitor featuring a processing system that receives a digital data stream from an ECG system. A cable houses the ECG system at one terminal end, and plugs into the processing system, which is typically worn on the patient's wrist like a conventional wristwatch. Specifically, the ECG system features: i) a connecting portion connected to multiple electrodes worn by the patient; ii) a differential amplifier that receives electrical signals from each electrode and process them to generate an analog ECG waveform; iii) an analog-to-digital converter that converts the analog ECG waveform into a digital ECG waveform; and iv) a transceiver that transmits a digital data stream representing the digital ECG waveform (or information calculated from the waveform) through the cable and to the processing system. Different ECG systems, preferably featuring three, five, or twelve electrodes, can be interchanged with one another.

In embodiments, the ECG system features a single-chip solution for determining ECG and IP waveforms, heart rate, respiratory rate, error codes, and diagnostic information such as ventricular tachycardia (VTAC), ventricular fibrillation (VFIB), and premature ventricular contractions (PVCs). A mechanical housing enclosing the ECG system can additionally house a motion-detecting sensor (e.g. a three-axis digital accelerometer) and a temperature sensor (e.g. a thermocouple). The cable features at least one conductor (and typically two conductors) that transmits both a first digital data stream representing the digital ECG waveform and a second digital data stream representing a digital motion waveform (e.g. an ACC waveform) generated by the accelerometer. Both digital data streams typically include a header portion indicating the source of the data stream, and a data portion that includes any relevant information. For the ECG system, such information includes an ECG waveform, heart rate, an error code, and a physiological state corresponding to the patient (e.g. VTAC, VFIB, PVCs). The data portion corresponding to the accelerometer includes information such as the ACC waveform, degree of motion, posture, and an activity level corresponding to the patient.

In another aspect, the system described above also features an oscillometry system that includes: i) a cuff, typically worn on the patient's arm to apply a pressure; ii) a pneumatic system that inflates the cuff and detects pressure therein to generate an analog oscillometric waveform; iii) an analog-to-digital converter that converts the analog oscillometric waveform into a digital oscillometric waveform; iv) a transceiver component that transmits a digital oscillometric data stream representing the digital oscillometric waveform (or values calculated therefrom) through a second serial port and to the processing system. In this case the digital oscillometry data stream features a header portion that indicates the origin of the packet, and a data portion that includes information such as a pressure waveform, blood pressure, heart rate, error codes, and a physiological state corresponding to the patient.

The system can also connect through one of its serial ports to an ancillary third system that can be, for example, a system that delivers a compound or other therapeutic intervention to the patient, or that can gather other data from the patient. Such systems include infusion pumps, insulin pumps, hemodialysis machines, glucometers, and systems for delivering oxygen, such as a mechanical ventilator. This list is not meant to be limiting. In the case of a therapeutic compound, the data portion of the packet can indicate the type of compound delivered to the patient, a dosage of the compound, and a rate of delivery of the compound. The third system can also be a sensor configured to measure a signal from the patient. Such sensors include, for example, a pulse oximeter, EEG monitor, temperature sensor, respiratory rate sensor, motion sensor, camera, impedance plethysmography sensor, optical spectrometer, and skin-conductance sensor. Again, this list is not meant to be limiting. Here, the data portion of the packet can include waveform information, heart rate, pulse rate, SpO2 value, EEG waveform, temperature, respiratory rate, degree of motion, posture, activity level, arm height, an image, a property of the patient measurable optically, and a property of the patient measurable electrically.

In embodiments, both the ECG and oscillometry systems include separate microprocessors, both of which are in communication with the processing system within the wrist-worn transceiver. For example, the processing system can send a packet (containing, e.g., a timing parameter) to the microprocessor within the ECG and oscillometry systems to synchronize them with the processing system worn on the wrist.

Preferably the transceiver component used in each of the above-described systems is a serial transceiver operating the Controller Area Network ("CAN") protocol. CAN is a multi-master broadcast serial bus standard for connecting electronic control units (ECUs). Each node is able to send and receive messages, but not simultaneously; a message, consisting primarily of an ID (usually chosen to identify the message-type/sender) and (up to eight) message bytes, is transmitted onto the bus and is sensed by all nodes. CAN transceivers associated with the ECG and pneumatic systems need to be synchronized to prevent any significant drift that may occur between the different time-domain waveforms they generate. This is typically done using a series of timing packets, described in detail below, that are sent between the wrist-worn transceiver and these remote systems.

In another aspect, the system provides a method for calculating blood pressure from a patient that features the following steps: (a) generating a first digital waveform indicating an ECG signal with a first remote sensor; (b) generating a second digital waveform indicating a pressure signal with a second remote sensor; (c) generating an analog waveform indicating an optical signal with a third remote sensor; (d) synchronizing the first digital waveform, the second digital waveform, and a digitized version of the analog waveform; (e) determining a pulse transit time from the first digital waveform and a digitized version of the analog waveform; (f) determining a calibration from the first digital waveform, the second digital waveform, and a digitized version of the analog waveform; and (g) determining a blood pressure value from the calibration and a pulse transit time.

Typically the optical signal is generated with an optical sensor configured to be worn around the patient's thumb. PTT is typically calculated from a time difference separating a QRS complex in the ECG waveform and a foot of a PPG waveform. In other embodiments the same optical sensor used to measure the optical waveform features a first LED operating in the red spectral range, and a second LED operating in the infrared spectral range. Optical waveforms measured with these LEDs can additionally be processed to determine SpO2, as is described in detail below.

The pressure signal is typically generated with a cuff-based pneumatic system wrapped around the patient's arm, and is typically measured during an inflation-based oscillometry measurement. Here, the processing component in the wrist-worn transceiver is further configured to calculate a calibration from a group of pulse transit times, wherein each pulse transit time in the group is measured when a different pressure is applied to the patient's arm. These data are then processed with a model that estimates an 'effective' blood pressure in the patient's arm during the inflation-based measurement, and uses this to estimate a relationship between PTT and blood pressure for the patient. This relationship represents a calibration that is then used with follow-on PTT measurements to measure the patient's cNIBP.

In another aspect, the invention provides a body-worn vital sign monitor featuring a processing component that includes a system for detecting an identifying code from a medical professional, and in response rendering a specific graphical user interface (GUI) on the wrist-worn transceiver. Preferably the system for detecting an identifying code is a barcode scanner, and the identifying code is a barcode printed on, e.g., the badge of the medical professional. Alternatively, a system based on radio-frequency identifying codes (RFID) is used in place of the barcode scanner. In still other embodiments the identifying code is simply an alphanumeric password entered into a GUI on the transceiver by the medical professional. In all cases, the identifying code prompts the transceiver to render a GUI that is appropriate for the medical professional, but not necessarily for the patient. Such a GUI may include, for example, time-domain waveforms, vital sign information, and parameters relating to alarms/alerts. The GUI for the patient is typically much simpler, and includes information such as the time of day and a 'nurse call' button. To support this feature, the wrist-worn transceiver typically includes a speaker and system for communicating over the hospital's wireless network using standard voice over IP (VOIP) protocols. The speaker can also play pre-recorded messages that may be germane to the patient.

The GUI displayed by the wrist-worn transceiver may depend on the orientation of the transceiver. This can be determined, for example, by signals generated by an internal accelerometer. For example, when the transceiver is oriented to face a medical professional, the accelerometer can generate representative signals that can be processed by an internal CPU, which in response will render a GUI suitable for the medical professional. Alternatively, the CPU will render a GUI suitable for the patient when signals from the accelerometer indicate that the transceiver is oriented towards the patient.

The wrist-worn transceiver can communicate with a remote device through a wireless connection that operates on the hospital's wireless network, or alternatively through a peer-to-peer connection. In another aspect of the invention, for example, the remote device is configured to simultaneously display vital signs for each patient in a group when a signal strength corresponding to each wrist-worn transceiver in the group is below a pre-determined threshold value. When the signal strength from the wireless system worn by a patient exceeds the pre-determine threshold, the remote monitor displays information for that particular patient. Such a situation would occur, for example, if a tablet computer normally disposed at a central nursing station was brought into the patient's room. Typically the pre-determined threshold value is between about −100 and −80 dB, and the wireless system used by each wrist-worn transceiver operates on an industry-standard communications protocol, preferably selected from 802.11, 802.15.4, and cellular wireless protocols. In embodiments, the remote device is a device comprising a microprocessor, a display, and a compatible communications transceiver. Examples include a computing device selected from the group consisting of a desktop computer, a portable computer, a tablet computer, a cellular telephone, and a personal digital assistant. This list is not meant to be limiting.

In yet another aspect, the invention provides a body-worn monitor featuring a 'hot swappable' battery. Here, the transceiver operates an algorithm that performs the following steps: (b) display on a GUI that the battery needs to be replaced; (c) detect when a secondary device is plugged into one of the serial ports, the secondary device indicating that the battery is about to be replaced; (d) store settings corresponding to the wireless system (e.g. IP and/or MAC addresses, passwords, encryption keys) and the patient's vital signs in the non-volatile memory; and (e) indicate on the GUI that the battery can be replaced. Once this is done, the depleted battery is replaced with a new one, and a button on the GUI is pressed to resume a wireless connection to the hospital's network. Continuous monitoring of the patient resumes once this is complete. Typically the secondary device plugs into a serial port on the transceiver, and sends a serial packet over the CAN bus indicating the battery is ready to be swapped.

The body-worn monitor can determine a patient's location in addition to their vital signs and motion-related properties. Typically, the location-determining sensor and the wireless transceiver operate on an industry-standard communications system, e.g. a wireless system based on 802.11, 802.15.4, or cellular protocols. In this case a location is determined by processing the wireless signal with one or more algorithms known in the art. These include, for example, triangulating signals received from at least three different wireless base stations, or simply estimating a location based on signal strength and proximity to a particular base station. In still other embodiments the location sensor includes a conventional global positioning system (GPS).

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a display wherein the user can select to display information (e.g. vital signs, location, and alarms) corresponding to a particular patient. This monitor can also include a voice interface so the medical professional can communicate with the patient.

Blood pressure is determined continuously and non-invasively using a technique, based on PTT, which does not require any source for external calibration. This technique, referred to herein as the 'Composite Technique', determines blood pressure using PPG, ECG, and OSC waveforms. The Composite Technique is described in detail in the patent application, the contents of which are fully incorporated herein by reference: VITAL SIGN M FOR MEASURING BLOOD PRESSURE USING OPTICAL, ELECTRICAL, AND PRESSURE WAVEFORMS (U.S. Ser. No. 12/138, 194; filed Jun. 12, 2008).

Still other embodiments are found in the following detailed description of the invention, and in the claims.

BRIEF DESCRIPTION OF THE DRAWINGS

FIG. 11 shows a schematic drawing of the ACC, ECG, pneumatic, and auxiliary systems of the body-worn monitor communicating over the CAN protocol with the wrist-worn transceiver;

FIG. 12A shows a three-dimensional view of the wrist-worn transceiver of FIG. 5C scanning a barcode printed on a badge of a medical professional;

FIG. 12B shows a patient view used in the GUI rendered on the wrist-worn transceiver of FIG. 12A;

FIG. 12C shows a medical professional view used in the GUI rendered on the wrist-worn transceiver of FIG. 12A;

DETAILED DESCRIPTION OF THE INVENTION

System Overview

Figure 1:
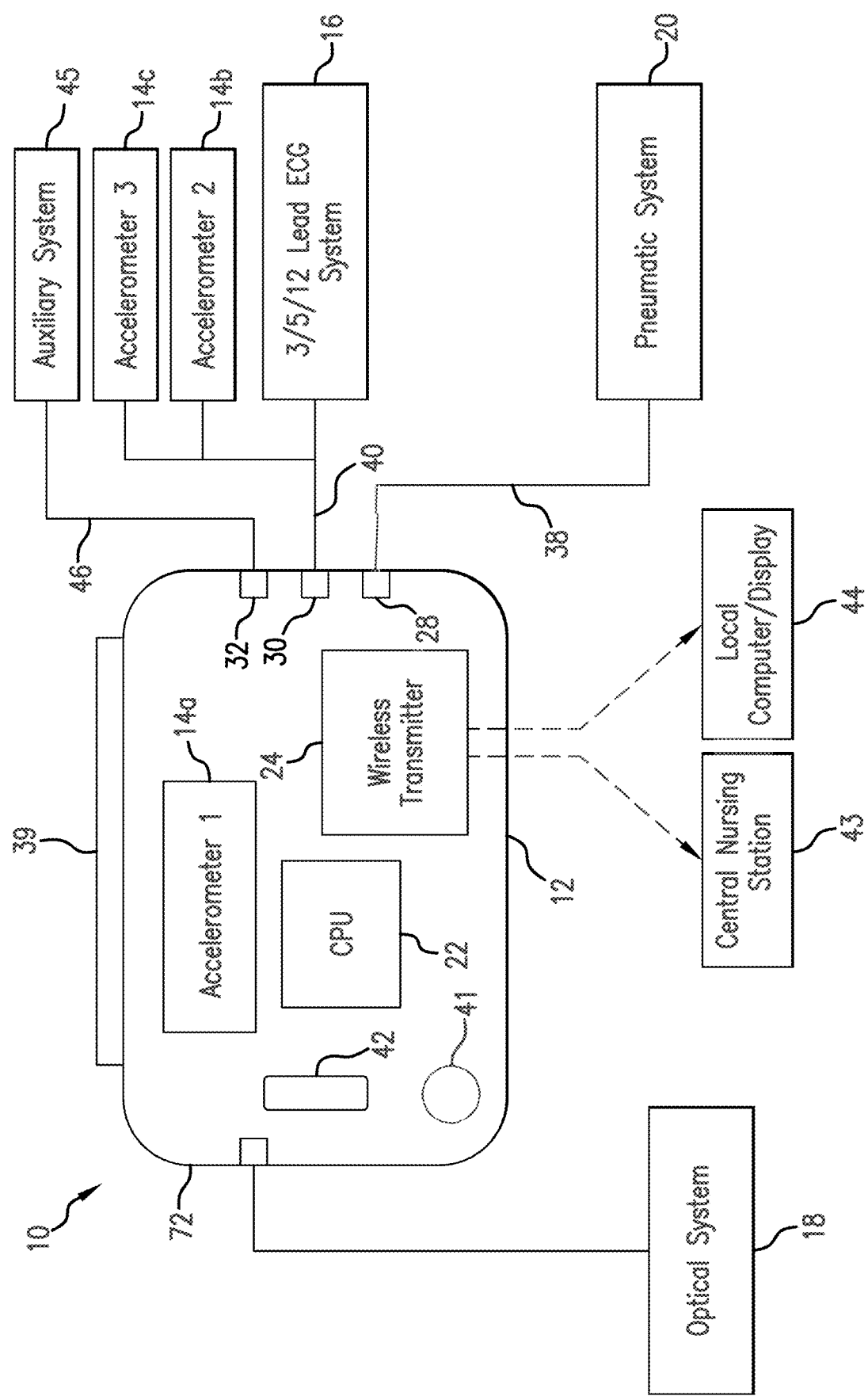
FIG. 1 shows a schematic drawing of a body-worn monitor featuring sensors for measuring ECG, PPG, ACC, OSC, and RR waveforms, and systems for processing these to determine a patient's vital signs.

FIG. 1 shows a schematic drawing of a body-worn monitor 10 according to the invention featuring a wrist-worn transceiver 72 that continuously determines vital signs (e.g. blood pressure, SpO2, heart rate, respiratory rate, and temperature) and motion-related properties (e.g. posture, arm height, activity level, and degree of motion) for an ambulatory patient in a hospital. The monitor 10 is small, lightweight, and comfortably worn on the patient's body during their stay in the hospital; its form factor is described in detail below. A medical professional can apply the monitor, for example, to a recently admitted patient waiting in the ED, and the same monitor can provide continuous monitoring during their stay in the hospital. For example, the patient can wear the monitor in their hospital room, as they receive specific procedures or tests, during transport to other rooms, and even during surgery. The monitor 10 provides continuous monitoring, and features a software framework that determines alarms/alerts if the patient begins to decompensate. The framework processes both the patient's motion and their vital sign information with algorithms that reduce the occurrence of false alarms.

A combination of features makes the body-worn monitor 10 ideal for ambulatory patients within the hospital. For example, its wrist-worn transceiver 72 features a wireless transmitter 24 that communicates through a hospital network to a computer (e.g. a portable tablet computer) at a central nursing station 43, and to a local computer 44 (e.g. a hand-held PDA) through a peer-to-peer connection. The specific mode of communication can be determined automatically (using, e.g., a signal strength associated with the wireless connection), or manually through an icon on the GUI.

The transceiver 72 features a CPU 22 that communicates through a digital CAN interface, or bus, to external systems featuring ECG 16, external accelerometers 14*b-c*, pneumatic 20, and auxiliary 45 sensors. Each sensor 16, 14*b-c*, 20, 45 is 'distributed' on the patient to minimize the bulk and weight normally associated with conventional vital sign monitors, which typically incorporate all electronics associated with measuring vital signs in a single plastic box. Moreover, each of these sensors 16, 14*b-c*, 20, 45 generate digital signals close to where they actually attach to the patient, as opposed to generating an analog signal and sending it through a relatively long cable to a central unit for processing. This can reduce noise due to cable motion which is often mapped onto analog signals. Cables 40, 38, 46 used in the body-worn monitor 10 to transmit packets over the CAN bus typically include 5 separate wires bundled together with a single protective cladding: the wires supply power and ground to the remote ECG system 16, accelerometers 14*b-c*, pneumatic 20, and auxiliary systems 45; provide high/low signal transmission lines for data transmitted over the CAN protocol; and provide a grounded electrical shield for each of these four wires. There are several advantages to this approach. First, a single pair of transmission lines in the cable (i.e. the high/low signal transmission lines) can transmit multiple digital waveforms generated by completely different sensors. This includes multiple ECG waveforms (corresponding, e.g., to vectors associated with three, five, and twelve-lead ECG systems) from the ECG circuit, along with ACC waveforms associated with the x, y, and z axes of accelerometers within the body-worn monitor 10. The same two wires, for example, can transmit up to twelve ECG waveforms (measured by a 12-lead ECG system), and six ACC waveforms (measured by the accelerometers 14*b-c*). Limiting the transmission line to a pair of conductors reduces the number of wires attached to the patient, thereby decreasing the weight and any cable-related clutter. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts.

The ECG 16, pneumatic 20, and auxiliary 45 systems are stand-alone systems that include a separate CPU, analog-to-digital converter, and CAN transceiver. During a measurement, they connect to the transceiver 72 through cables 40, 38, 46 and connectors 30, 28, 32 to supply digital inputs over the CAN bus. The ECG system 16, for example, is completely embedded in a terminal portion of its associated cable. Systems for three, five, and twelve-lead ECG monitoring can be swapped in an out simply by plugging the appropriate cable (which includes the ECG system 16) into a CAN connector 30 on the wrist-worn transceiver 72, and the attaching associated electrodes to the patient's body.

The wrist-worn transceiver 72 renders separate GUIs that can be selected for a particular viewer, e.g., different displays directed to the patient as compared to a medical professional. To do this, the transceiver 72 includes a barcode scanner 42 that can scan an identifying barcode printed, e.g., on the medical professional's badge, which indicates the viewer's identity or type to the system. In response, the system renders a GUI featuring information (e.g. vital signs, waveforms) tailored for the indicated viewer; that is, a medical professional can receive information on the GUI that may not be suitable for viewing by the patient. So that the patient can communicate with the medical professional, the transceiver 72 includes a speaker 41 interfaced to the CPU 22 and wireless system 24 that allows the patient to communicate with a remote medical professional using a standard VOIP protocol. A Li:ion battery 39 powers the transceiver 72 for about four days on a single charge, and can be removed in a 'hot swap' manner so that after the battery change the transceiver remains wirelessly connected to the hospital's network and no information is lost. This is done simply by plugging a specialized 'dongle' into the CAN connector 32 for the auxiliary system 45, replacing the battery 39, and then removing the dongle.

Three separate digital accelerometers 14*a-c* are non-obtrusively integrated into the monitor's form factor; two of them 14*b-c* are located on the patient's body, separate from the wrist-worn transceiver 72, and send digitized, motion-related information through the CAN bus to the CPU 22. The first accelerometer 14*a* is mounted on a circuit board within the transceiver 72, and monitors motion of the patient's wrist. The second accelerometer 14*b* is incorporated directly into the cable 40 connecting the ECG system 16 to the transceiver 72 so that it can easily attach to the patient's bicep and measure motion and position of the patient's upper arm. As described below, this can be used to compensate for hydrostatic forces associated with changes in the patient's arm height that affect the monitor's blood pressure measurement, and can be additionally used to calibrate the monitor's blood pressure measurement through the patient's 'natural' motion. The third accelerometer 14c is typically mounted to a circuit board that supports the ECG system 16 on the terminal end of the cable, and typically attaches to the patient's chest. Motion and position of the patient's chest can be used to determine their posture and activity states, which as described below can be used with vital signs for generating alarm/alerts. Each accelerometer 14a-c measures three unique ACC waveforms, each corresponding to a separate axis (x, y, or z) representing a different component of the patient's motion. To determine posture, arm height, activity level, and degree of motion, the transceiver's CPU 22 processes signals from each accelerometer 14a-c with a series of algorithms, described in the following patent applications, the contents of which are incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). In total, the CPU 22 can process nine unique, time-dependent signals ($ACC_{1-9}$) corresponding to the three axes measured by the three separate accelerometers. Algorithms determine parameters such as the patient's posture (e.g., sitting, standing, walking, resting, convulsing, falling), the degree of motion, the specific orientation of the patient's arm and how this affects vital signs (particularly blood pressure), and whether or not time-dependent signals measured by the ECG 16, optical 18, or pneumatic 20 systems are corrupted by motion.

To determine blood pressure, the transceiver 72 processes ECG and PPG waveforms measured, respectively, by the ECG 16 and optical 18 systems. The optical system 18 features a thumb-worn sensor that includes LEDs operating in the red ($\lambda$∥660 nm) and infrared ($\lambda$∥900 nm) spectral regions, and a photodetector that detects their radiation after it passes through arteries within the patient's thumb. The ECG waveform, as described above, is digitized and sent over the CAN interface to the wrist-worn transceiver 72, while the PPG waveform is transmitted in an analog form and digitized by an analog-to-digital converter within the transceiver's circuit board. The pneumatic system 20 provides a digitized pressure waveform and oscillometric blood pressure measurements (SYS, DIA, and MAP) through the CAN interface; these are processed by the CPU 22 to make cuff-based 'indexing' blood pressure measurements according to the Composite Technique. The indexing measurement typically only takes about 40-60 seconds, after which the pneumatic system 20 is unplugged from its connector 28 so that the patient can move within the hospital without wearing an uncomfortable cuff-based system.

Collectively, these systems 14a-c, 16, 18, and 20 continuously measure the patient's vital signs and motion, and supply information to the software framework that calculates alarms/alerts. A third connector 32 also supports the CAN bus and is used for auxiliary medical devices (e.g. a glucometer, infusion pump, system for end-tidal CO2) that is either worn by the patient or present in their hospital room.

Once a measurement is complete, the transceiver 72 uses an internal wireless transmitter 24 to send information in a series of packets to a remote monitor 43, 44 within the hospital. The wireless transmitter 24 typically operates on a protocol based on 802.11, and can communicate with a computer located at a central nursing station 43 through an existing network within the hospital, or through a peer-to-peer connection to a local computer or display 44 (e.g. a PDA worn by a medical professional). Information transmitted by the transceiver alerts the medical professional if the patient begins to decompensate. A server connected to the hospital network typically generates this alarm/alert once it receives the patient's vital signs, motion parameters, ECG, PPG, and ACC waveforms, and information describing their posture, and compares these parameters to preprogrammed threshold values. As described in detail below, this information, particularly vital signs and motion parameters, is closely coupled together. Alarm conditions corresponding to mobile and stationary patients are typically different, as motion can corrupt the accuracy of vital signs (e.g., by adding noise), and induce artificial changes in them (e.g., through acceleration of the patient's heart and respiratory rates) that may not be representative of the patient's actual physiology.

Measuring Time-Dependent Physiological Signals with the Body-Worn Monitor

Figure 3:
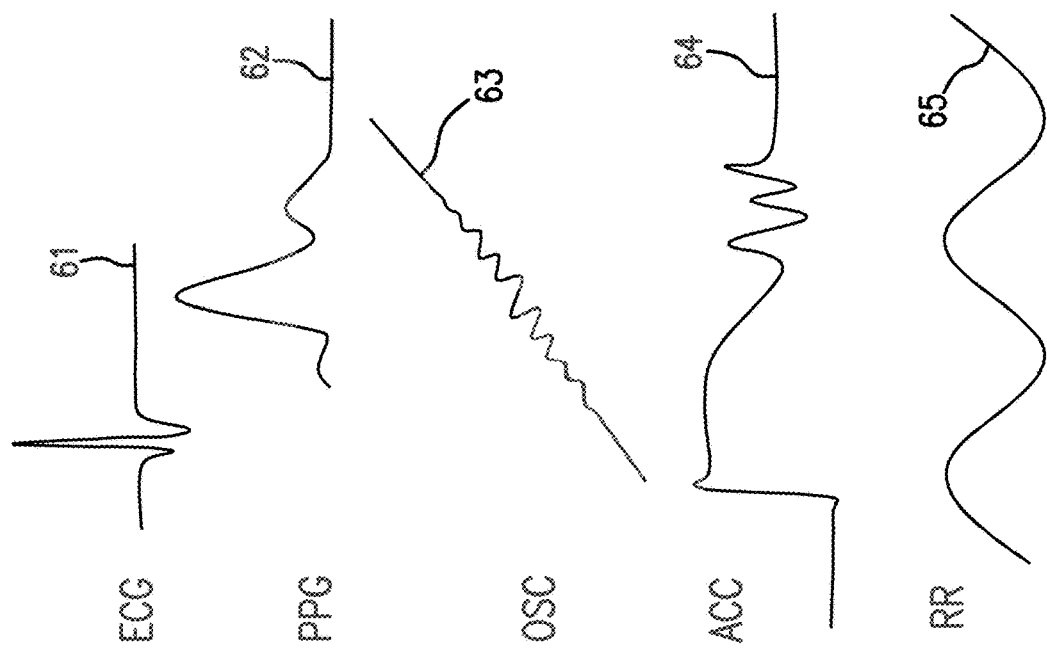
FIG. 3 is a graph of time-dependent ECG, PPG, OSC, ACC, and RR waveforms generated with the body-worn monitor and sensors of FIG. 2.
Figure 2:
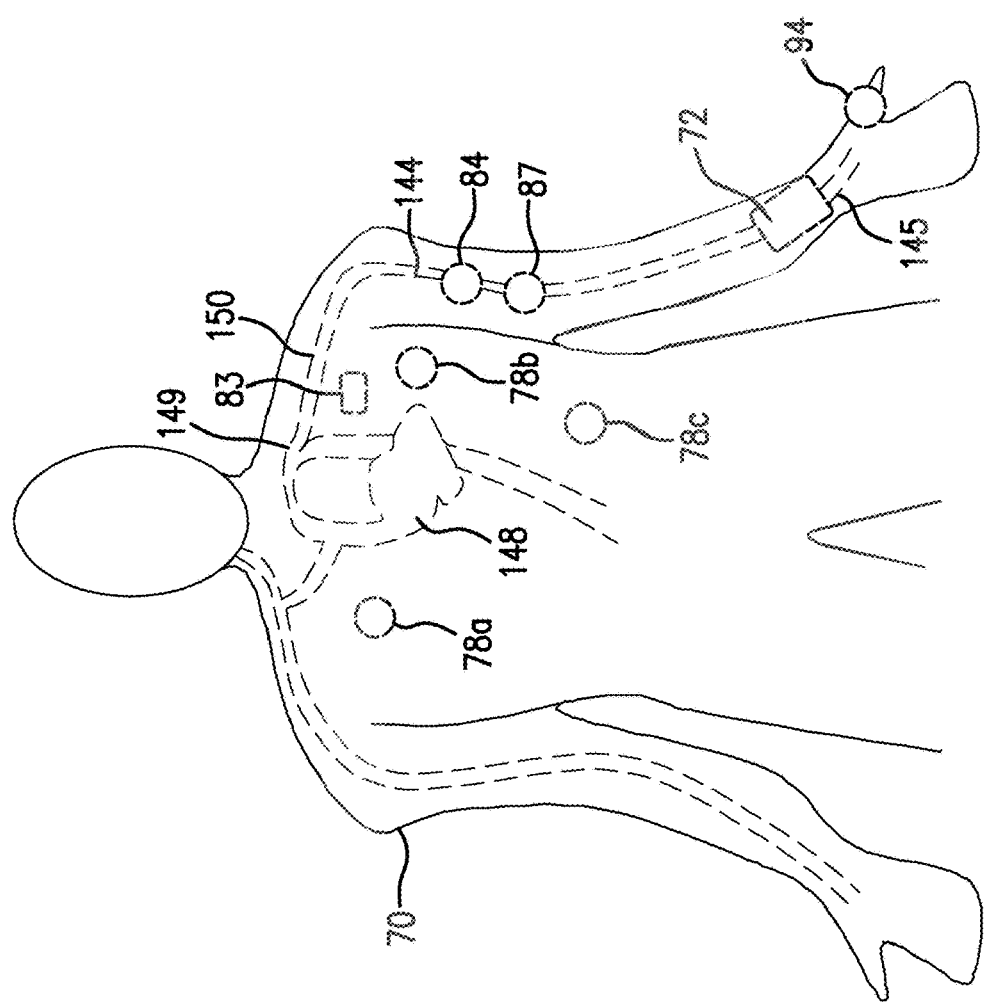
FIG. 2 shows a schematic drawing of a patient wearing the body-worn monitor of FIG. 1 and its associated sensors.

FIGS. 2 and 3 show how a network of sensors 78a-c, 83, 84, 87, 94 within the body-worn monitor 10 connect to a patient 70 to characterize them within a hospital. During a measurement, the sensors 78a-c, 83, 84, 87, 94 measure signals that are processed by the monitor 10 to generate time-dependent ECG 61, PPG 62, OSC 63, ACC 64, and RR 65 waveforms. These, in turn, yield the patient's vital signs and motion parameters. Each waveform 61-65 relates to a unique physiological characteristic of the patient 70. For example, each of the patient's heartbeats generates electrical impulses that pass through the body near the speed of light, along with a pressure wave that propagates through the patient's vasculature at a significantly slower speed. Immediately after the heartbeat, the pressure wave leaves the heart 148 and aorta 149, passes through the subclavian artery 150 to the brachial artery 144, and from there through the radial and ulnar arteries 145 to smaller arteries in the patient's fingers. Three disposable electrodes 78a-c attached to the patient's chest measure unique electrical signals which pass to a single-chip ECG circuit 83 that terminates a distal end of the ECG cable. Typically, these electrodes attach to the patient's chest in a conventional 'Einthoven's triangle' configuration featuring three unique 'vectors', each corresponding to a different lead (e.g. LEAD 1, II, II). Related configurations can also be used when five and twelve-lead ECG systems are used in place of the three-lead system, as described below with reference to FIGS. 7A,B. Within the ECG circuit 83 signals are processed using an amplifier/filter circuit and analog-to-digital converter to generate a digital ECG waveform 61 corresponding to each lead. The ECG waveform 61 features a sharp, well-defined QRS complex corresponding to each heartbeat; this marks the initiation of the patient's cardiac cycle. Heart rate is determined directly from the ECG waveform 61 using known algorithms, such as those described in the following reference, the contents of which are incorporated herein by reference: 'ECG Beat Detection Using Filter Banks', Afonso et al., *IEEE Trans. Biomed Eng.*, 46:192-202 (1999).

To generate an IP waveform, one of the ECG electrodes in the circuit 78a is a 'driven lead' that injects a small amount of modulated current into the patient. A second, non-driven electrode 78c, typically located on the opposite side of the torso, detects the current, which is further modulated by capacitance changes in the patient's chest cavity resulting from breathing. Further processing and filtering of the IP waveforms yields an oscillating RR waveform 65 which can be further processed to calculate respiratory rate.

The optical sensor 94, described in detail with reference to FIGS. 9A,B, features two LEDs and a single photodetector that collectively measure a time-dependent PPG waveform 62 corresponding to each of the LEDs. The sensor and algorithms for processing the PPG waveforms are described in detail in the following patent application, the contents of which are fully incorporated herein by reference: BODY-WORN PULSE OXIMETER (U.S. Ser. No. 61/218, 062; filed Jun. 17, 2009). The waveform 62 represents a time-dependent volumetric change in vasculature (e.g. arteries and capillaries) that is irradiated with the sensor's optical components. Volumetric changes are induced by a pressure pulse launched by each heartbeat that travels from the heart 148 to arteries and capillaries in the thumb according to the above-describe arterial pathway. Pressure from the pressure pulse forces a bolus of blood into this vasculature, causing it to expand and increase the amount of radiation absorbed, and decrease the transmitted radiation at the photodetector. The pulse shown in the PPG waveform 62 therefore represents the inverse of the actual radiation detected at the photodetector. It follows the QRS complex in the ECG waveform 61, typically by about one to two hundred milliseconds. The temporal difference between the peak of the QRS complex and the foot of the pulse in the PPG waveform 62 is the PTT, which as described in detail below is used to determine blood pressure according to the Composite Technique. PPG waveforms generated by both the red and infrared LEDs are also processed by the CPU within the wrist-worn transceiver to determine SpO2, as is described in detail in the above-mentioned patent application. PTT-based measurements made from the thumb yield excellent correlation to blood pressure measured with a femoral arterial line. This provides an accurate representation of blood pressure in the central regions of the patient's body.

Each accelerometer generates three time-dependent ACC waveforms 64, corresponding to the x, y, and z-axes, which collectively, indicate the patient's motion, posture, and activity level. The body-worn monitor, as described above, features three accelerometers that attach to the patient: one in the wrist-worn transceiver 72, one in the ECG circuit 83, and one near the bicep 87 that is included in the cable connecting these two components. The frequency and magnitude of change in the shape of the ACC waveform 64 indicate the type of motion that the patient is undergoing. For example, the waveform 64 can feature a relatively time-invariant component indicating a period of time when the patient is relatively still, and a time-variant component when the patient's activity level increases. Magnitudes of both components will depend on the relationship between the accelerometer and a gravity vector, and can therefore be processed to determine time-invariant features, such as posture and arm height. A frequency-dependent analysis of the time-variant components yields the type and degree of patient motion. Analysis of ACC waveforms 64 is described in detail in the above-mentioned patent applications, the contents of which have been fully incorporated herein by reference.

The OSC waveform 63 is generated from the patient's brachial artery 144 with the pneumatic system and a cuff-based sensor 84 during the pressure-dependent portion of the Composite Technique. It represents a time-dependent pressure, measured during inflation, which is applied to the brachial artery and measured by a digital pressure sensor within the pneumatic system. The waveform 63 is similar to waveforms measured during deflation by conventional oscillometric blood pressure monitors. For the Composite Technique, however, the waveform 63 is typically measured as the cuff gradually inflates, as is described in detail in the following patent application, the contents of which have been previously incorporated herein by reference: VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008).

During a measurement, the pressure waveform 63 increases in a mostly linear fashion as pressure applied by the cuff 84 to the brachial artery 144 increases. When it reaches a pressure slightly below the patient's diastolic pressure, the brachial artery 144 begins to compress, resulting in a series time-dependent pulsations caused by each heartbeat that couple into the cuff 84. The pulsations modulate the OSC waveform 63 with an amplitude that varies in a Gaussian-like distribution, with maximum modulation occurring when the applied pressure is equivalent to the patient's MAP. The pulsations can be filtered out and processed using digital filtering techniques, such as a digital bandpass filter that passes frequencies ranging from 0.5-20 Hz. The resulting waveform can be processed to determine SYS, DIA, and MAP, as is described in detail in the above-referenced patent application, the contents of which have been previously incorporated herein by reference. The cuff 84 and pneumatic system are removed from the patient's bicep once the pressure-dependent component of the Composite Technique is complete.

The high-frequency component of the OSC waveform 63 (i.e. the pulses) can be filtered out to estimate the exact pressure applied to the patient's brachial artery during oscillometry. According to the Composite Technique, PTT measured while pressure is applied will gradually increase as the brachial artery is occluded and blood flow is gradually reduced. The pressure-dependent increase in PTT can be fit with a model to estimate the patient-specific relationship between PTT and blood pressure. This relationship, along with SYS, MAP, and DIA determined from the OSC waveform during inflation-based oscillometry, is used during the Composite Technique's pressure-free measurements to determine blood pressure directly from PTT.

There are several advantages to making the indexing measurement during inflation, as opposed to deflation. Measurements made during inflation are relatively fast and comfortable compared to those made during deflation. Inflation-based measurements are possible because of the Composite Technique's relatively slow inflation speed (typically 5-10 mmHg/second) and the high sensitivity of the pressure sensor used within the body sensor. Such a slow inflation speed can be accomplished with a small pump that is relatively lightweight and power efficient. Moreover, measurements made during inflation can be immediately terminated once systolic blood pressure is calculated. This tends to be more comfortable than conventional cuff-based measurements made during deflation. In this case, the cuff typically applies a pressure that far exceeds the patient's systolic blood pressure; pressure within the cuff then slowly bleeds down below the diastolic pressure to complete the measurement.

A digital temperature sensor proximal to the ECG circuit 83 measures the patient's skin temperature at their torso. This temperature is an approximation of the patient's core temperature, and is used mostly for purposes related to trending and alarms/alerts.

Hardware System for Body-Worn Monitor

Figures 4A, 4B:
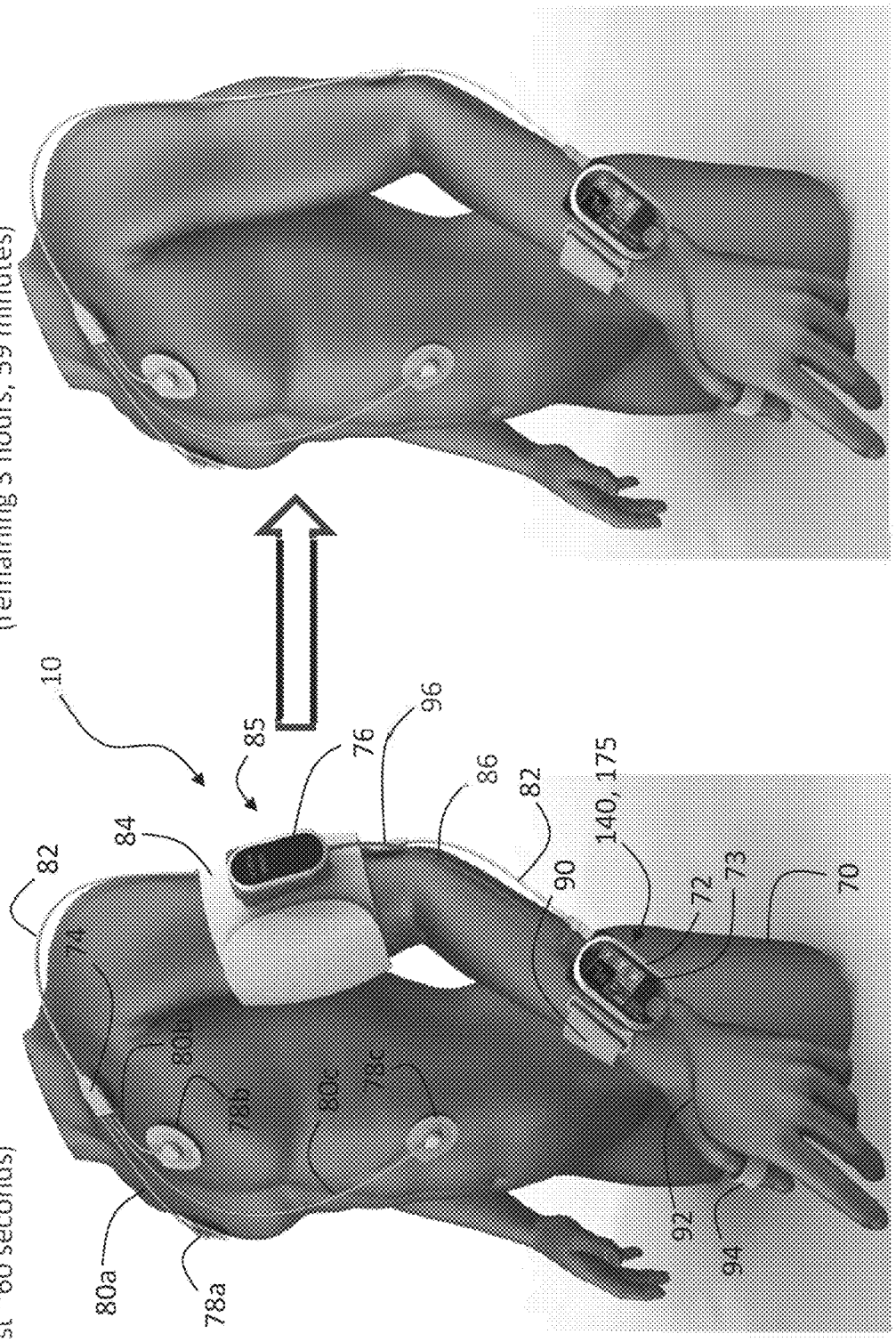
FIG. 4A shows a three-dimensional images of the body-worn monitor of FIG. 1 attached to a patient with a cuff-based pneumatic system used for a calibrating indexing measurement.
FIG. 4B shows a three-dimensional image of the body-worn monitor of FIG. 1 attached to a patient without a cuff-based pneumatic system used for a calibrating indexing measurement.

FIGS. 4A and 4B shows the specific form factor of the exemplary body-worn monitor 10 described in FIGS. 1 and 2, and how the monitor 10 attaches to a patient 70. Two configurations of the system are shown with these figures: FIG. 4A shows the system used during the pressure-dependent indexing portion of the Composite Technique, and includes a pneumatic, cuff-based system 85 attached to the patient's bicep; FIG. 4B shows the system used for subsequent SpO2 and cNIBP measurements, which rely solely on PTT. The indexing measurement typically takes about 60 seconds, and is typically performed once at the beginning of a measurement, and every 4-8 hours afterwards. Once the indexing measurement is complete the cuff-based system 85 is typically removed from the patient. The remainder of the time the monitor 10 measures other vital signs and cNIBP according to the Composite Technique.

The body-worn monitor 10 features a wrist-worn transceiver 72 with a touch panel interface 73 that displays numerical values for all the vital signs. A wrist strap 90 affixes the transceiver 72 to the patient's wrist like a conventional wristwatch. A five-wire cable 92 connects the transceiver 72 to an optical sensor 94 that wraps around the base of the patient's thumb. During a measurement, the optical sensor 94 generates a time-dependent PPG which is processed along with an ECG to measure cNIBP and SpO2, as described above.

To determine ACC waveforms the body-worn monitor 10 features three separate accelerometers located at different portions on the patient's arm and chest. The first accelerometer is surface-mounted on a circuit board in the wrist-worn transceiver 72 and measures signals associated with movement of the patient's wrist. As described above, this motion can also be indicative of that originating from the patient's fingers, which will affect both the SpO2 and cNIBP measurements. The second accelerometer is included in a small bulkhead portion 96 included along the span of the cable 82. During a measurement, a small piece of disposable tape, similar in size and shape to a conventional bandaid, affixes the bulkhead portion 96 to the patient's arm. In this way the bulkhead portion 96 serves two purposes: 1) it measures a time-dependent ACC waveform from the mid-portion of the patient's arm, thereby allowing their posture and arm height to be determined as described above; and 2) it secures the cable 82 to the patient's arm to increase comfort and performance of the body-worn monitor 10, particularly when the patient is ambulatory.

The cuff-based module 85 features a pneumatic system 76 that includes a pump, manifold, two solenoid valves, pressure fittings, pressure sensor, analog-to-digital converter, microcontroller, and rechargeable Li:ion battery. These components are described in more detail with reference to FIG. 8A-C. During an indexing measurement, the pneumatic system 76 inflates a disposable cuff 84 and performs the indexing measurement according to the Composite Technique, described above. The cuff 84 attached to the pneumatic system 76 is typically disposable and features an internal, airtight bladder that wraps around the patient's bicep to deliver a uniform pressure field. A pneumatic fitting on the cuff's outer surface snaps into a pressure fitting so that the pneumatic system sits flat against the cuff to simplify application and make the system as low-profile as possible. During the indexing measurement, pressure values are digitized by the internal analog-to-digital converter, and sent through a cable 86 according to the CAN protocol, along with SYS, DIA, and MAP blood pressures and any error codes, to the wrist-worn transceiver 72 for processing. Once the cuff-based measurement is complete, the cuff-based module 85 is removed from the patient's arm and the cable 86 is disconnected from the wrist-worn transceiver 72. cNIBP is then determined using PTT, as described in detail above.

Figure 7A:
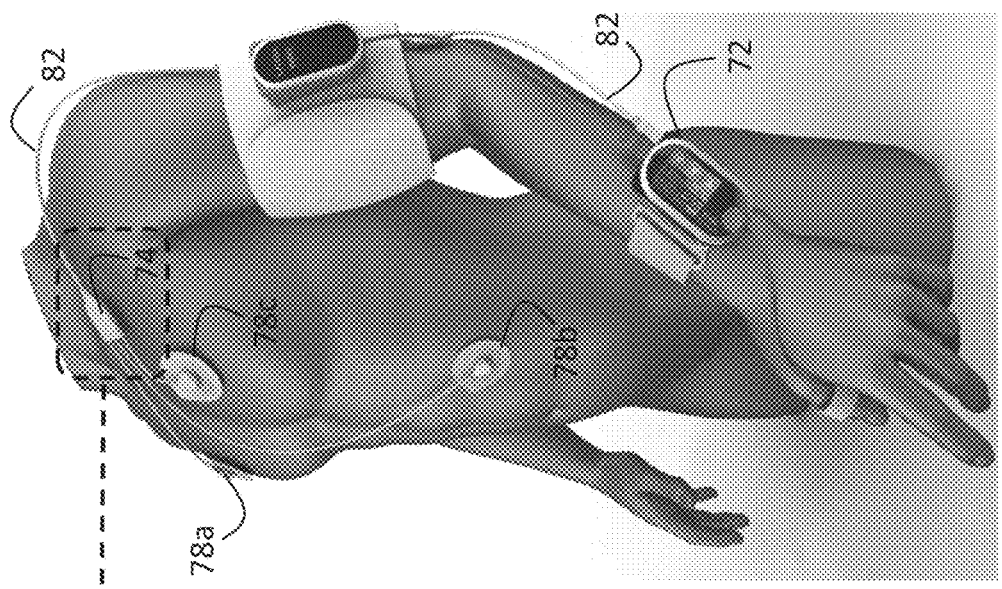
FIG. 7A shows a three-dimensional image of the body-worn monitor of FIG. 4B attached to a patient along with the ECG system.

To determine an ECG, the body-worn monitor 10 features a small-scale, three-lead ECG circuit integrated directly into a bulkhead 74 that terminates an ECG cable 82. The ECG circuit features an integrated circuit that collects electrical signals from three chest-worn ECG electrodes 78a-c connected through cables 80a-c. FIGS. 7A,B describe these systems in more detail. From these electrical signals the ECG circuit determines up to three ECG waveforms, each corresponding to a different lead, which are digitized using an analog-to-digital converter within the integrated circuit, and sent through the cable 82 to the wrist-worn transceiver 72 according to the CAN protocol. The bulkhead 74 also includes an accelerometer that measures motion associated with the patient's chest as described above, as well as a thermocouple to measure skin temperature.

Figure 5A:
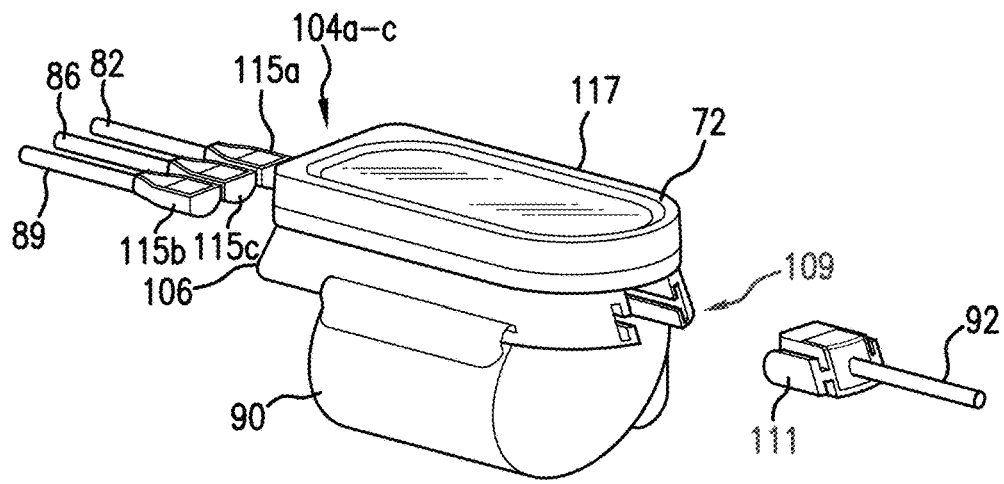
FIG. 5A shows a three-dimensional images of the wrist-worn transceiver before receiving cables from other sensors within the body-worn monitor.
Figure 5B:
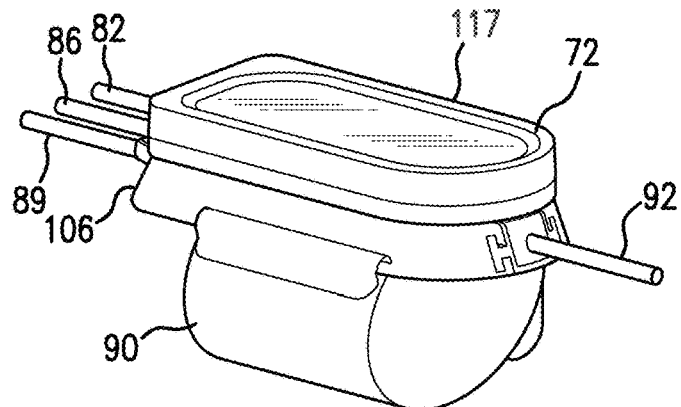
FIG. 5B shows a three-dimensional image of the wrist-worn transceiver after receiving cables from other sensors within the body-worn monitor.

FIGS. 5A, 5B show three-dimensional views of the wrist-worn transceiver 72 before and after receiving cables 82, 86, 89 from sensors worn on the patient's upper arm and torso, as well as the cable 92 that connects to the optical sensor. The transceiver 72 is sealed in a water-proof plastic casing 117 featuring electrical interconnects (not shown in the figure) on its bottom surface that interface to the terminal ends 111, 115a-c of cables 82, 86, 89, 92 leading to the monitor's various sensors. The electrical interconnects support serial communication through the CAN protocol, described in detail herein, particularly with reference to FIG. 11. During operation, the transceiver's plastic casing 117 snaps into a plastic housing 106, which features an opening 109 on one side to receive the terminal end 111 of the cable 92 connected to the optical sensor. On the opposing side the plastic housing 106 features three identical openings 104a-c that receive the terminal ends 115a-c of cables 82, 86, 89 connected to the ECG and accelerometer systems (cable 82), the pneumatic cuff-based system (cable 86), and ancillary systems (cable 89) described above. In addition to being waterproof, this design facilitates activities such as cleaning and sterilization, as the transceiver contains no openings for fluids common in the hospital, such as water and blood, to flow inside. During a cleaning process the transceiver 72 is simply detached from the plastic housing 106 and then cleaned.

Figure 5C:
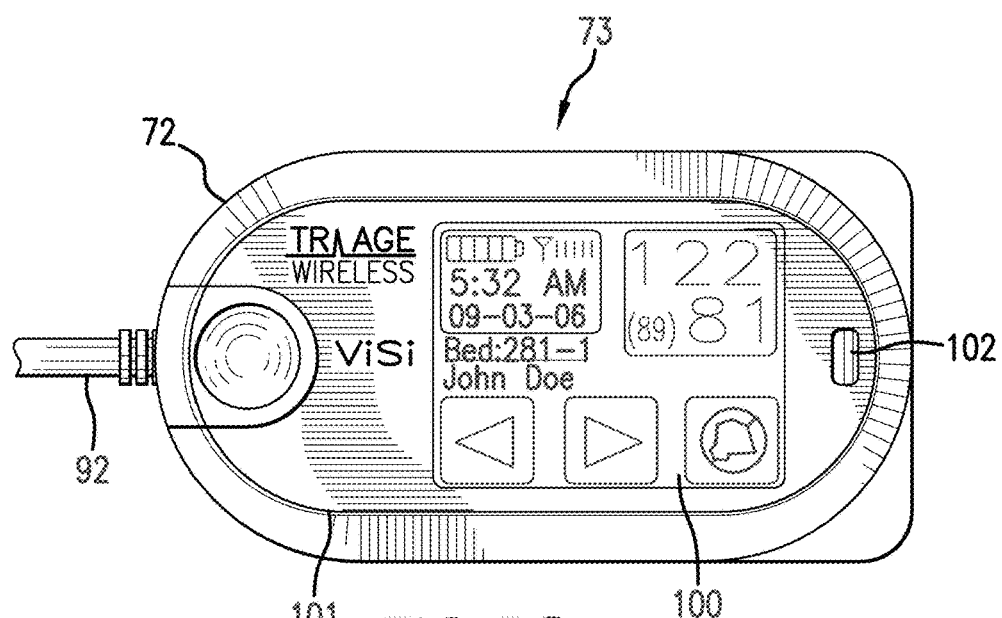
FIG. 5C shows a top view of the wrist-worn transceiver of FIGS. 5A and 5B rendering a GUI.

The transceiver 72 attaches to the patient's wrist using a flexible strap 90 which threads through two D-ring openings in the plastic housing 106. The strap 90 features mated Velcro patches on each side that secure it to the patient's wrist during operation. The transceiver 72 houses the circuits 175, 140 described in FIGS. 9B and 10 and, as shown in FIG. 5C, additionally features a touchpanel display 100 that renders a GUI 73. The GUI 72, for example, can be altered de on the viewer (typically the patient or a medical professional). These features are described in more detail with reference to FIGS. 12A-12C.

The electrical interconnects on the transceiver's bottom side line up with the openings 104a-c, and each supports the CAN protocol to relay a digitized data stream to the transceiver's internal CPU. The protocol for this process is described in detail with reference to FIG. 11. This allows the CPU to easily interpret signals that arrive from the monitor's body-worn sensors, and means that these connectors are not associated with a specific cable. Any cable connecting to the transceiver 72 can be plugged into any opening 104a-c. As shown in FIG. 5A, the first opening 104a receives the cable 82 that transports digitized ECG waveforms determined from the ECG circuit and electrodes, and digitized ACC waveforms measured by accelerometers in the cable bulkhead and the bulkhead portion associated with the ECG cable 82.

The second opening 104b receives the cable 86 that connects to the pneumatic cuff-based system used for the pressure-dependent indexing measurement. This connector receives a time-dependent pressure waveform delivered by the pneumatic system to the patient's arm, along with values for SYS, DIA, and MAP values determined during the indexing measurement. The cable 86 unplugs from the opening 104b once the indexing measurement is complete, and is plugged back in after approximately four hours for another indexing measurement.

The final opening 104c can be used for an auxiliary device, e.g. a glucometer, infusion pump, body-worn insulin pump, ventilator, or end-tidal CO2 monitoring system. As described with reference to FIG. 11, digital information generated by these systems will include a header that indicates their origin so that the CPU can process them accordingly.

The transceiver includes a speaker 101 that allows a medical professional to communicate with the patient using a voice over Internet protocol (VOIP). For example, using the speaker 101 the medical professional can query the patient from a central nursing station or mobile phone connected to a wireless, Internet-based network within the hospital. Or the medical professional can wear a separate transceiver similar to the one shown in FIGS. 5A-C, and use this as a communication device. In this application, the transceiver 72 worn by the patient functions much like a conventional cellular telephone or 'walkie talkie': it can be used for voice communications with the medical professional and can additionally relay information describing the patient's vital signs and motion.

Figure 6A:
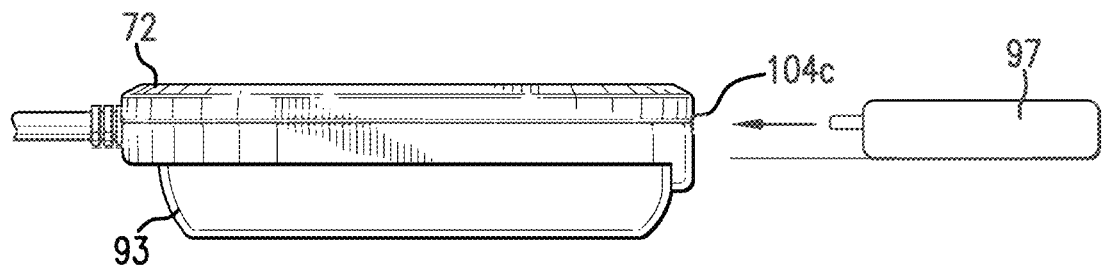
FIG. 6A shows a side view of the wrist-worn transceiver of FIGS. 5A-C before a battery hot swap.
Figure 6B:
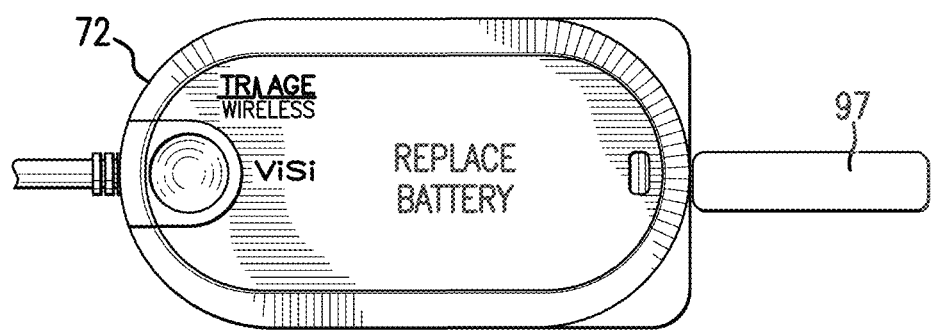
FIG. 6B shows a top view of the wrist-worn transceiver of FIGS. 5A-C during a battery hot swap.
Figure 6C:
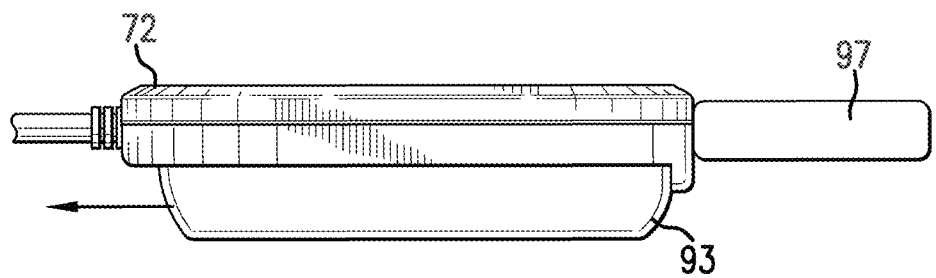
FIG. 6C shows a side view of the wrist-worn transceiver of FIGS. 5A-C during a battery hot swap.
Figure 6D:
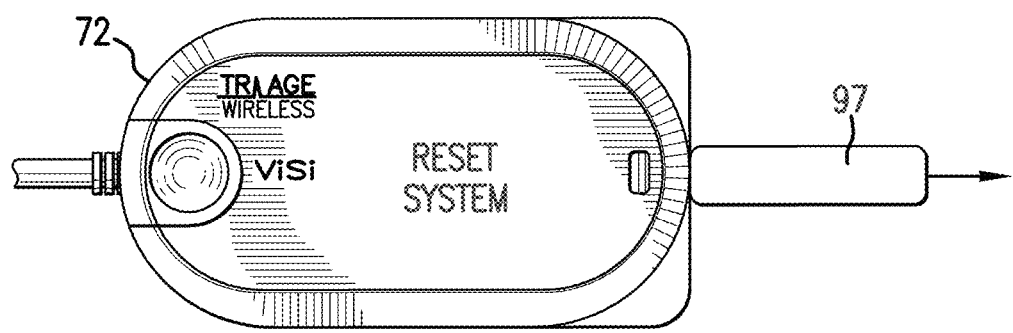
FIG. 6D shows a top view of the wrist-worn transceiver of FIGS. 5A-C after a battery hot swap.

FIGS. 6A-6D show, respectively, side (6A,C) and top (6B,D) views of the wrist-worn transceiver 72, and indicate how the Li:ion battery 93 can be removed using a 'hot swap' configuration so that the transceiver's data and wireless connection to the network are preserved after the battery change. Prior to the hot swap a battery-powered dongle 97 operating a firmware program is plugged into one of the openings 104c, as indicated by FIG. 6A. After being plugged in, the dongle 97 sends a packet formatted according to the CAN protocol to the transceiver indicating that its battery is about to be replaced with one having a full charge. The transceiver receives the packet, and in response stores in non-volatile memory information that is normally not present when a device is initially powered on. This includes the patient's vital signs, cNIBP indexing parameters, trending information, and parameters concerning the transceiver's connection to the hospital network. Alternatively this information can be temporarily stored in a data buffer on the network, or on non-volatile memory associated with the dongle. Once this is complete, as indicated in FIG. 6B, the transceiver's GUI renders a message that the battery 93 may be replaced. The depleted battery 93, located on the bottom side of the transceiver 72, can now be replaced with a charged battery. As shown in FIG. 6D, after this operation is complete the GUI renders a virtual button that, once pressed, will reset the transceiver 72 to return it to its configuration before the battery swap. The transceiver then downloads the above-described information stored in either internal non-volatile memory, on the network, or in the dongle 97, and then the dongle 97 is removed from the opening 104c. The transceiver 72 then returns to monitoring the patient.

Configurable ECG System

FIGS. 7A, B show a configurable ECG system 74 integrated within the body-worn monitor and can accommodate three, five, or twelve lead ECG configurations. The figure shows a system that includes three leads. As described above, the entire ECG system 74, including systems for differentially amplifying, filtering, and digitizing ECG signals, is mounted on a circuit board disposed at a distal end of the ECG cable 82. Preferably this system is based on a single ASIC which is a small-scale, low-power, single-chip solution and can be easily incorporated in the form factor shown in FIG. 7A. Alternatively the ECG system can be composed of a series of discrete components making up the system's requisite filters and amplifiers. Using the CAN protocol, the ECG system 74 sends digital ECG information (e.g. ECG waveforms corresponding to each lead, heart rate and respiratory rate values, error codes) in the form of packets to the wrist-worn transceiver 72. All ECG information is processed and digitized before being transmitted, which means a low-profile, five-wire cable 82 is adequate for three, five, and twelve-lead ECG systems. These different systems are typically embedded in unique cables, which can be easily swapped in and out and applied to the patient, and are labeled appropriately. A medical professional can incorporate them into the body-worn monitor simply by plugging the desired cable into any CAN connector on the wrist-worn transceiver 72, and then attaching the appropriate ECG leads to the patient. The ECG system sends packets indicating how many leads it includes to the transceiver, which then processes this information accordingly.

Figure 7B:
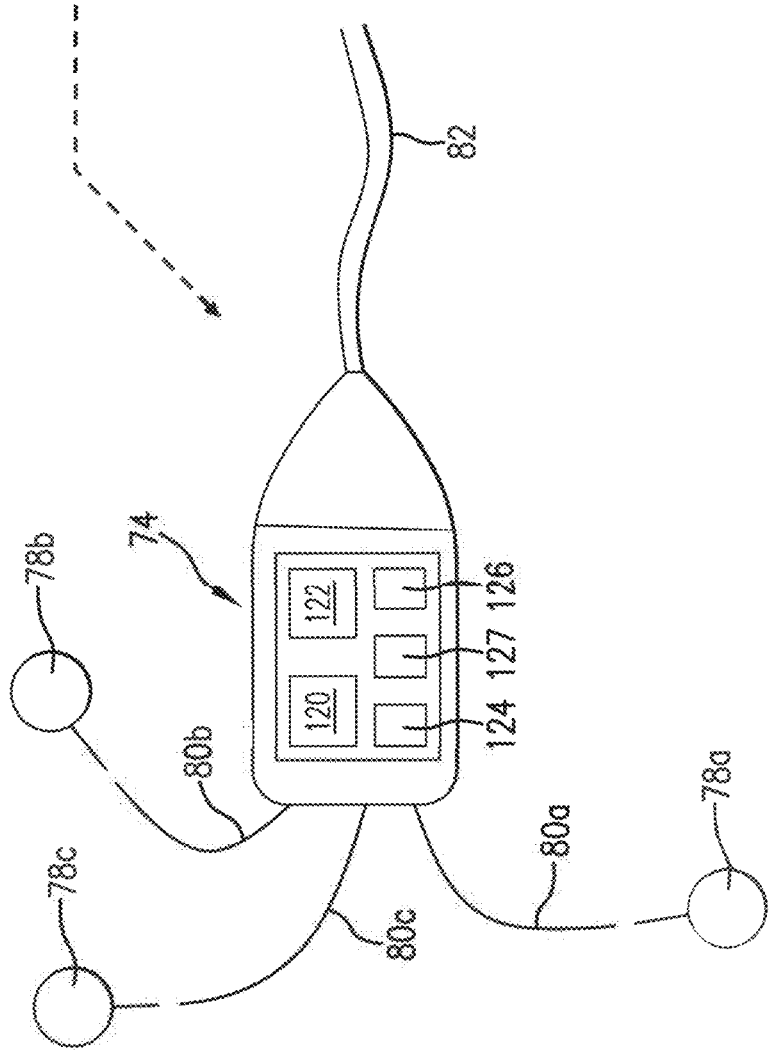
FIG. 7B shows a schematic drawing of the ECG system within the body-worn monitoring of FIG. 7A.

FIG. 7B shows a high-level schematic drawing of a three-lead ECG system 74 that connects to the wrist-worn transceiver 72 in FIG. 7A. The ECG system 75 includes three electrode lead wires 80a-c that connect, respectively, to separate electrodes 78a-c. These are typically disposable adhesive electrodes worn on the patient's chest in an Einthoven's triangle configuration, as shown in FIG. 7A. During a measurement, each electrode 78a-c measures a unique electrical signal from the patient's chest which then propagates through the lead wires 80a-c to the single-chip ECG processor 120, described above. The ECG processor 120 differentially amplifies the ECG signals from each electrode 78a-c, and then filters and further amplifies the resulting waveform according to parameters which can be configured with a microcontroller 122 within the ECG system 74. The microcontroller 122 interfaces to a crystal 126 (typically operating at 100 kHz) and a clock divider 127 that processes incoming timing packets, as is described in more detail below with reference to FIG. 11. The ECG processor 120 includes an internal analog-to-digital converter that digitizes unique waveforms corresponding to each lead. It then processes the digitized waveforms to determine heart rate and parameters describing the patient's cardiac condition, e.g. VTAC, VFIB, and PVCs. The ECG processor 120 can also drive one of the electrodes (e.g. electrode 78a) with a modulated current, as described above, and detect this current along with breathing-induced modulations with a second electrode (e.g. electrode 78b) to determine respiratory rate according to impedance pneumography.

Once this information is determined, a CAN controller 124 within the ECG circuit 74 processes the resulting data and transmits it as a series of CAN packets to the wrist-worn transceiver 72, described in detail below. Values for heart rate, respiratory rate, and one of the time-dependent ECG waveforms (typically the Lead II waveform), along with alarms/alerts related to cardiac parameters such as VTAC, VFIB, and PVCs, are then displayed on the transceiver's GUI. One of the ECG waveforms is processed to determine blood pressure according to the Composite Technique. The transceiver 72 relays all the information it receives from the ECG system 74 to a server connected to the in-hospital network.

Removable Pneumatic System

Figure 8A:
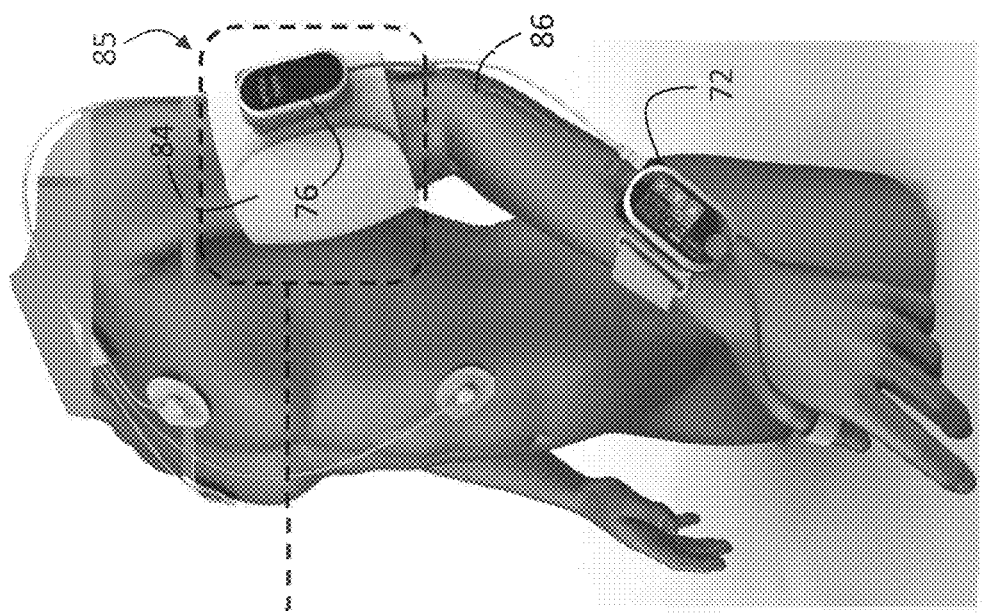
FIG. 8A shows a three-dimensional image of the body-worn monitor of FIG. 4B attached to a patient along with the cuff-based pneumatic system.
Figure 8B:
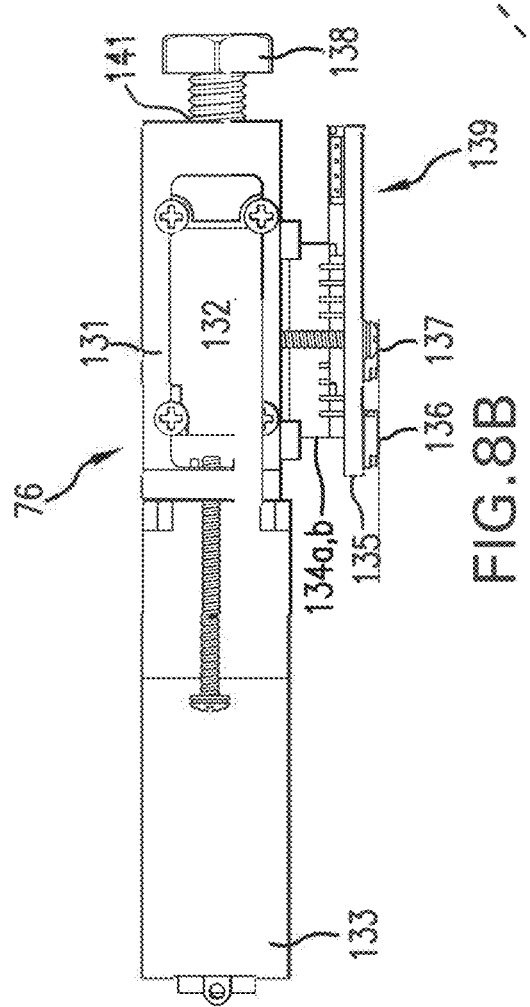
FIG. 8B shows a side view of the pneumatic components with the cuff-based pneumatic system of FIG. 8A.
Figure 8C:
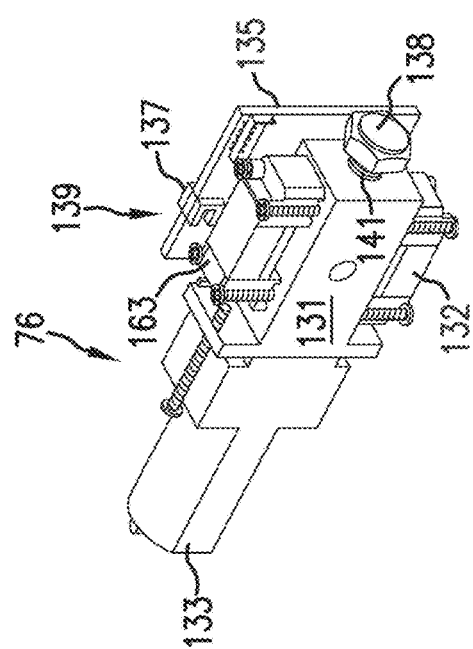
FIG. 8C shows a three-dimensional view of the pneumatic components with the cuff-based pneumatic system of FIG. 8A.

FIGS. 8A-C show an exemplary cuff-based system 85 used within the body-worn sensor to make pressure-dependent measurements according to the Composite Technique. Within the cuff-based system 85 is a pneumatic system 76 featuring a single motherboard 135 that includes components 139 similar to those shown in FIG. 7B (microcontroller, crystal oscillator, clock divider, CAN transceiver) to process pressure-dependent waveforms and communicate with the wrist-worn transceiver 72. To power these components, the pneumatic system 76 additionally includes a separate Li:ion battery (not shown in the figure) that connects through connector 137. This battery is similar to that used in the transceiver 72. A CAN connector 136 receives the cable 86 so that the pneumatic system 76 can transmit information to the wrist-worn transceiver 72.

To measure the pressure waveform during a pressure-dependent measurement, the pneumatic system 76 features a small mechanical pump 133 that inflates a bladder within the cuff 84, which is worn around the patient's bicep and features a pneumatic connector (not shown in the figure) that the pneumatic system 76 plugs into. The system 76 features two solenoid valves 132, 163, each controlled by a separate microcontroller mounted on the motherboard, and configured to connect the pump 133 to an outside air reservoir to inflate the cuff. Both solenoid valves 132, 163 and the pump 133 connect through a manifold 131 to an opening 141 that attaches through a connector (not shown in the figure) to the bladder within the armband, and additionally to a pair of pressure sensors 134a,b that sense the pressure in the bladder. The opening 141 is covered by a screw-in plug 138 to prevent build up of debris in the manifold 131 when the pneumatic system 76 is not attached to the cuff 84. A primary solenoid valve 132 is normally closed when not activated (i.e., when power is not applied). The secondary solenoid valve 163 has the opposite configuration, and is normally open when not activated. When both valves 132, 163 are activated (i.e., when power is applied), the primary valve 132 opens and the secondary valve 163 closes, thus providing a path for the pump 133 to funnel air through the manifold 131 and to the cuff 84. During a measurement, heartbeat-induced pulsations couple into the bladder as it inflates, and are subsequently mapped onto a pressure waveform. The pressure sensors 134a,b generate digital pressure waveforms which are filtered and processed by the microcontroller to measure blood pressure during inflation, as described above. The first pressure sensor 134a generates a pressure waveform that is used for the cuff-based indexing measurement, while the second sensor 134b is used as a back-up in case the first sensor 134a fails. Once complete, blood pressure values are used to index the PTT-based pressure-free measurements as described above. When the measurement is complete, the valves 132, 163 are deactivated, and the pump 133 is no longer powered, causing the cuff 84 to rapidly deflate. The cuff 84 and cuff-based system 85 is then removed, and follow-on cNIBP measurements are calculated from PTT as described above.

Optical Sensor for cNIBP and SpO2

Figure 9A:
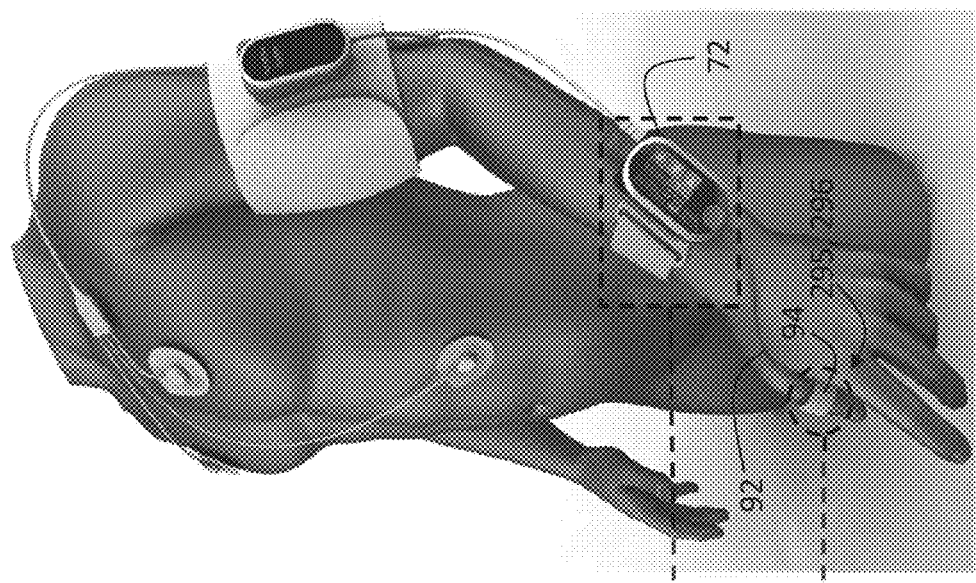
FIG. 9A shows a three-dimensional image of the body-worn monitor of FIG. 4B attached to a patient along with the thumb-worn optical sensor.

FIGS. 9A,B show an exemplary optical sensor 94 that measures PPG signals from both red and infrared LEDs which the wrist-worn transceiver 72 processes to determine cNIBP and SpO2. The sensor 94 includes a dual LED 150 operating at 660 and 905 nm, de on the direction of bias, a photodetector 155 for detecting radiation from the LED 150 after it passes through a portion of the patient's thumb, and a laser-trimmed resistor 149 indicating the specific wavelength of the red portion of the dual LED 150, as described below. Powering these components is a circuit 175 within the wrist-worn transceiver that generates time-dependent current pulses to drive the LEDs. The circuit 175 features an operational amplifier 180 that receives a control voltage ($V_{control}$) on its gating pin. The amplifier 180 is connected to a transistor 182 and resistor 181 that, along with a supply voltage of 3.3V (typically from a Li:ion battery), generate the current pulses used to drive the dual LED 150. To select the biasing direction of the LED, and thus choose the wavelength that is emitted, the circuit 175 features red control lines 185, 190 and infrared control lines 187, 189 that connect directly to I/O lines in the CPU within the wrist-worn transceiver. During a measurement, current pulses flow from the 3.3V supply voltage, across one direction of the LED 150, and ultimately through the transistor 182 and resistor 181 to ground 183. The LED 150 is biased in a forward direction when control lines 185, 190 are toggled closed, thereby supplying a drive current pulse of $i_{LED}=V_{control}/R_1$ to the LED 150 to generate red radiation. Voltage flowing across the LED 150 is also decreased because it is a diode. In this case the control lines 187, 189 for infrared radiation are left open. This configuration persists for 100 μs, after which the red control lines 185, 190 are switched closed, and the infrared control lines 187, 189 are switched open. This biases the LED 150 in a backwards direction to generate infrared radiation according to the above-described drive current. The alternating process is repeated at 500 Hz.

During a measurement, the CPU in the wrist-worn transceiver determines the value of the resistor 149 by monitoring a voltage drop across it; this value, in turn, is compared to a value stored in memory to select the appropriate coefficients relating a parameter called a 'ratio of ratios' (RoR) to SpO2. This calculation is described in detail in the above-referenced patent application describing SpO2, the contents of which have been incorporated herein by reference. The probe 94 generates alternating red and infrared radiation at 500 Hz that passes through the base of the patient's thumb 151, where it is partially absorbed by underlying vasculature according to the patient's heart rate and SpO2 values. Radiation that transmits through the thumb 151 illuminates a photodiode 155 that, in response, generates a photocurrent varying in magnitude with the degree of optical absorption in the patient's thumb. An amplifier circuit 140 beginning with a transimpedance amplifier 156 receives the photocurrent and converts it to a corresponding voltage which is then amplified and filtered to generate the PPGs waveforms with both red and infrared wavelengths used to determine SpO2 and cNIBP.

Figure 9B:
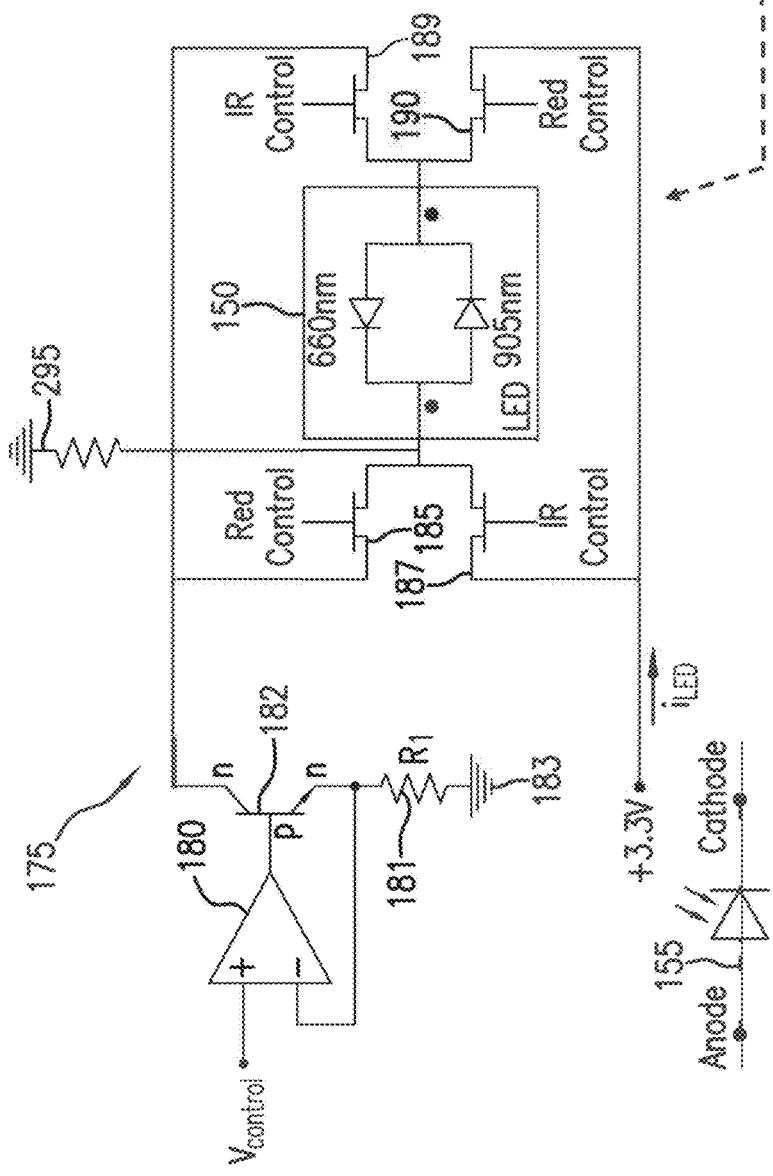
FIG. 9B is a schematic circuit diagram of the thumb-worn optical sensor of FIG. 9A and the switching components used to control its light-emitting diodes (LEDs)
Figure 10:
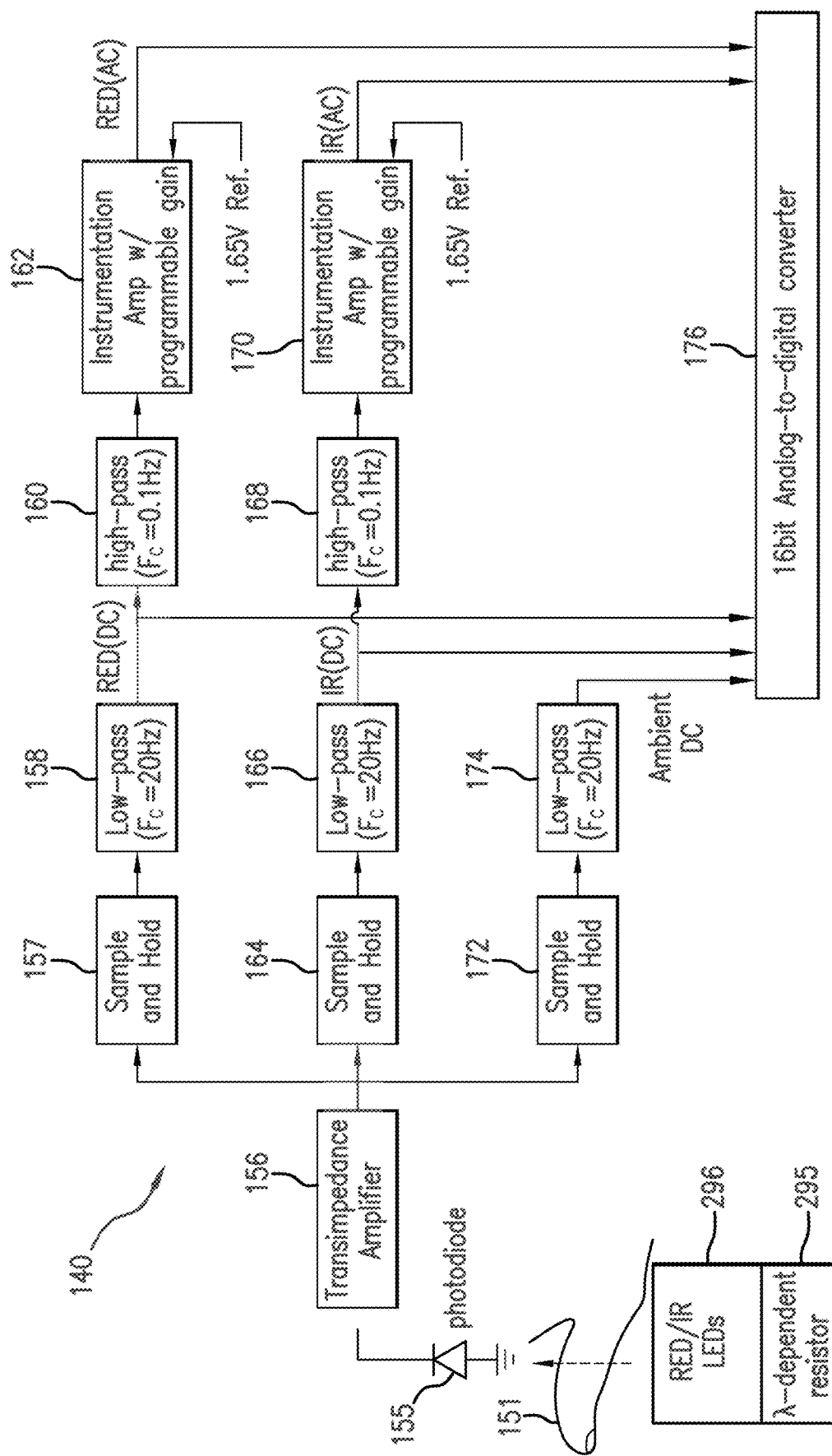
FIG. 10 is a schematic circuit diagram of the amplifier/filter circuit used to process signals from the thumb-worn optical sensor shown in FIG. 9B.

The amplifier circuit 140 features separate channels for amplifying and filtering signals corresponding to red radiation, infrared radiation, and ambient light detected by the photodiode 155 when the LED is not biased to generate radiation. This occurs, for example, during the time periods when neither the red or infrared LED is driven. Once detected, the degree of ambient light can be subtracted from both the red and infrared signals to improve their resultant signal-to-noise ratio. The amplifier channel corresponding to red radiation is activated by a sample-and-hold integrated circuit 157 that is controlled by the same control lines 185, 190 that drive the red LED, as shown in FIG. 9B. When the red LED is driven, the sample-and-hold circuit 157 is switched on, while similar components 164, 172 corresponding to the infrared signals and ambient light are switched off. The sample-and-hold circuit 157 samples and maintains an analog voltage from the transimpedance amplifier 156, which then passes through a low-pass filter 158 characterized by a 20 Hz cutoff. This filter removes any high-frequency noise (e.g. 60 Hz electrical noise) that is not related to the PPG waveform, and yields a preliminary waveform that is digitized with an analog-to-digital converter 176, and processed as described above to generate a DC portion of the PPG. The preliminary waveform then passes through a high-pass filter 160 with a cutoff of 0.1 Hz to remove the DC portion and leave only the AC portion, which typically represents about 0.5-1% of the total signal magnitude. The AC portion is further amplified with a standard instrumentation amplifier 162 featuring a programmable gain that is controlled with a 1.65 reference voltage and a digital potentiometer (not shown in the figure; this component may be included directly in the instrumentation amplifier) featuring a variable resistance controlled by the CPU within the wrist-worn transceiver. The CPU selects the resistance (according to a predetermined command) and corresponding gain to maximize the dynamic range of the analog-to-digital converter 176. This process results in an amplified version of the AC portion of the red PPG waveform, which is then digitized with the analog-to-digital converter 176 and then processed as described above.

The above-described filtering and amplification processes are repeated when the infrared LED and a sample-and-hold integrated circuit 164 corresponding to the infrared channel are activated with infrared control lines 187, 189. The low-pass 166 and high-pass 168 filters corresponding to this channel are identical to those used for the red channel. The instrumentation amplifier 170 is also identical, but is controlled by a separate digital potentiometer to have a unique, uncoupled gain. This is because the infrared PPG waveform typically has a relatively large amplitude, and thus requires less amplification, than the red PPG waveform. The channel corresponding to ambient light only requires processing of DC signals, and thus includes a sample-and-hold integrated circuit 172 that passes an analog voltage to a low-pass filter 174 featuring a 20 Hz cutoff. The filtered value corresponding to ambient light is then digitized with the analog-to-digital converter and then processed as described above.

A five-wire cable, similar to that used for the ECG and pneumatic systems, connects the thumb-worn optical sensor to the wrist-worn transceiver. Black circles in FIG. 9B indicate where wires in the cable connect to circuit elements in the thumb-worn sensor (only four dots are shown; the fifth connection is a conducting shield for the remaining 4 wires). Note that the value for the laser-trimmed resistor is determined by a voltage drop when both control lines for the red 185, 190 and infrared 187, 189 are open. In this configuration there is no bias across the LED, so radiation is not emitted, but there is a small voltage drop across the infrared control lines 187, 189 due to the resistor 149. The resistor value is chosen to be sufficiently small so that only a small amount of current is drawn during an actual measurement.

Communicating with Multiple Systems Using the CAN Protocol

As described above, the ECG, ACC, and pneumatic systems within the body-worn system can send digitized information to the wrist-worn transceiver through the CAN protocol. FIG. 11 shows a schematic drawing indicating how CAN packets 201a-d, 212a-e transmitted between these systems facilitate communication. Specifically, each of the ACC 14, ECG 74, pneumatic 76, and auxiliary 45 systems include a separate analog-to-digital converter, microcontroller, frequency-generating crystal oscillator (typically operating at 100 kHz), and real-time clock divider that collectively generate and transmit digital data packets 201a-d according to the CAN protocol to the wrist-worn transceiver 72. Each crystal uses the internal real-time clock on the internal microprocessor within the respective system. This allows the microcontroller within each system to be placed in a low-power state in which its real-time operating system (RTOS) dispatch system indicates that it is not ready to run a task. The real-time clock divider is programmed to create an interrupt which wakes up the microcontroller every 2 milliseconds.

The wrist-worn transceiver 72 features a 'master clock' that generates real-time clock 'ticks' at the sampling rate (typically 500 Hz, or 2 ms between samples). Each tick represents an incremented sequence number. Every second, the wrist-worn transceiver 72 transmits a packet 212e over the CAN bus that digitally encodes the sequence number. One of the criteria for accurate timing is that the time delay between the interrupt and the transmission of the synchronizing packet 212e, along with the time period associated with the CAN interrupt service routine, is predictable and stable. During initialization, the remote CAN buses do not sleep; they stay active to listen for the synchronization packet 212e. The interrupt service routine for the synchronization packet 212e then establishes the interval for the next 2 millisecond interrupt from its on-board, real-time crystal to be synchronized with the timing on the wrist-worn transceiver 72. Offsets for the packet transmission and interrupt service delays are factored into the setting for the real-time oscillator to interrupt synchronously with the microprocessor on the wrist-worn transceiver 72. The magnitude of the correction factor to the real-time counter is limited to 25% of the 2 millisecond interval to ensure stability of this system, which represents a digital phase-locked loop.

When receipt of the synchronization packet 212e results in a timing correction offset of either a 0, +1, or −1 count on the remote system's oscillator divider, software running on the internal microcontroller declares that the system is phase-locked and synchronized. At this point, it begins its power-down operation and enables measurement of data as described above.

Each remote system is driven with a 100 kHz clock, and a single count of the divider corresponds to 20 microseconds. This is because the clock divider divides the real-time clock frequency by a factor of 2. This is inherent in the microcontroller to ensure that the clock has a 50% duty cycle, and means the clock can drift+/−20 microseconds before the actual divider chain count will disagree by one count, at which time the software corrects the count to maintain a phase-locked state. There is thus a maximum of 40 microseconds of timing error between data transmitted from the remote systems over the CAN bus. Blood pressure is the one vital sign measured with the body-worn monitor that is calculated from time-dependent waveforms measured from different systems (e.g. PPG and ECG waveforms). For this measurement, the maximum 40-microsecond timing error corresponds to an error of +/−0.04 mmHg, which is well within the error (typically +/−5 mmHg) of the measurement.

In order to minimize power consumption, the wrist-worn transceiver 72 and remote systems 14, 74, 76, 45 power down their CAN bus transceivers between data transfers. During a data transfer, each system generates a sequence number based on the synchronization packet 212e, and includes this in its packet. The sequence number represents the interval between data transfers in intervals of 2 milliseconds. It is a factor of 500 (e.g. 2, 4, 5, 10) that is the number of 2 millisecond intervals between transfers on the CAN bus. Each remote system enables its CAN bus during the appropriate intervals and sends its data. When it has finished sending its data, it transmits a 'transmit complete' packet indicating that the transmission is complete. When a device has received the 'transmit complete' packet it can disable its CAN transceiver to further reduce power consumption.

Software in each of the ACC 14, ECG 74, pneumatic 76, and auxiliary 45 systems receive the sequence packet 212e and the corresponding sequence number, and set their clocks accordingly. There is typically some inherent error in this process due to small frequency differences in the crystals (from the ideal frequency of 100 kHz) associated with each system. Typically this error is on the order of microseconds, and has only a small impact on time-dependent measurements, such as PTT, which are typically several hundred milliseconds.

Once timing on the CAN bus is established using the above-described procedure, each of the ACC 14, ECG 74, and pneumatic 76 systems generate time-dependent waveforms that are transmitted in packets 201a-d, each representing an individual sample. Each packet 201a-d features a header portion which includes the sequence number 212a-d and an initial value 210a-d indicating the type of packet that is transmitted. For example, accelerometers used in the body-worn system are typically three-axis digital accelerometers, and generate waveforms along the x, y, and z-axes. In this case, the initial value 210a encodes numerical values that indicate: 1) that the packet contains ACC data; and 2) the axis (x, y, or z) over which these data are generated. Similarly, the ECG system 204 can generate a time-dependent ECG waveform corresponding to Lead I, II, or III, each of which represents a different vector measured along the patient's torso. Additionally, the ECG system 204 can generate processed numerical data, such as heart rate (measured from time increments separating neighboring QRS complexes), respiratory rate (from an internal impedance pneumography component), as well as alarms calculated from the ECG waveform that indicate problematic cardiovascular states such as VTAC, VFIB, and PVCs. Additionally, the ECG system can generate error codes indicating, for example, that one of the ECG leads has fallen off. The ECG system typically generates an alarm/alert, as described above, corresponding to both the error codes and potentially problematic cardiovascular states. In this case, the initial value 210b encodes numerical values that indicate: 1) that the packet contains ECG data; 2) the vector (Lead I, II, or III) corresponding to the ECG data; and 3) an indication if a cardiovascular state such as VTAC, VFIB, or PVCs was detected by the ECG system.

The pneumatic system 76 is similar to the ECG system in that it generates both time-dependent waveforms (i.e. a pressure waveform, measured during oscillometry, characterizing the pressure applied to the arm and subsequent pulsations measured during an oscillometric measurement) and calculated vital signs (SYS, DIA, and MAP measured during oscillometry). In some cases errors are encountered during the oscillometric blood pressure measurement. These include, for example, situations where blood pressure is not accurately determined, an improper OSC waveform, overinflation of the cuff, or a measurement that is terminated before completion. In these cases the pneumatic system 76 generates a corresponding error code. For the pneumatic system 76 the initial value 210c encodes numerical values that indicate: 1) that the packet contains blood pressure data; 2) an indication that the packet includes an error code.

In addition to the initial values 210a-d, each packet 201a-d includes a data field 214a-d that encodes the actual data payload. Examples of data included in the data fields 214a-d are: 1) sampled values of ACC, ECG, and pressure waveforms; 2) calculated heart rate and blood pressure values; and 3) specific error codes corresponding to the ACC 14, ECG 74, pneumatic 76, and auxiliary 25 systems.

Upon completion of the measurement, the wrist-worn transceiver 72 receives all the CAN packets 201a-d, and synchronizes them in time according to the sequence number 212a-d and identifier 210a-d in the initial portions 216 of each packet. Every second, the CPU updates the time-dependent waveforms and calculates the patient's vital signs and motion-related properties, as described above. Typically these values are calculated as a 'rolling average' with an averaging window ranging from 10-20 seconds. The rolling average is typically updated every second, resulting in a new value that is displayed on the wrist-worn transceiver 72. Each packet received by the transceiver 72 is also wirelessly retransmitted as a new packet 201b' to a remote computer 43 connected to an in-hospital network. The new packet 201b' includes the same header information 210b', 212b' and data field information 214b' as the CAN packets transmitted between systems within the body-worn monitor. Also transmitted are additional packets encoding the cNIBP, SpO2, and processed motion states (e.g. posture, activity level, degree of motion), which unlike heart rate and SYS, DIA, and MAP are calculated by the CPU in the wrist-worn transceiver. Upon receipt of the packet 201b', the remote computer 43 displays vital signs, waveforms, motion information, and alarms/alerts, typically with a large monitor that is easily viewed by a medical professional. Additionally the remote computer 43 can send information through the hospital network (e.g. in the case of an alarm/alert), and store information in an internal database.

Displaying Information Using Graphical User Interfaces

Referring to FIGS. 12A-C, the transceiver 72 features a touchpanel display 100 that renders a multi-window GUI 73 which can be tailored to both medical professionals and the patient. To select the appropriate GUI, the transceiver 72 includes a small-scale infrared barcode scanner 102 that emits radiation 120 to scan a barcode 122 worn on a badge 121 of a medical professional. Information encoded on the barcode 122 is compared to a database stored within the transceiver 72 to indicate, for example, that a nurse or doctor is viewing the user interface. This database can be updated through the hospital's network. In response, the GUI 73 displays vital sign data, waveforms, alarms/alerts and other medical diagnostic information appropriate for medical professionals, as shown by the screen 126 in FIG. 12B. Using this GUI 73, the medical professional can view the vital sign information, set alarm parameters, and enter information about the patient (e.g. their posture, demographic information, medication, or medical condition). The nurse can press a 'Patient View' button on the GUI 73 indicating that these operations are complete. The patient view is shown by the screen 125 in FIG. 12C, and purposefully lacks any content related to vital signs. Instead is designed to be relatively generic, featuring the time, date, and icons indicating the patient's activity level, whether or not an alarm has been generated, battery life, and wireless signal strength. The GUI also features a graphical 'call nurse' button that, once depressed, wirelessly sends a signal to the central nursing station indicating that the patient needs assistance from a nurse. The patient view screen 125 includes a button labeled 'UNLOCK' that, once activated, allows a nurse or doctor to activate the medical professional view 126 shown in FIG. 11B. Tapping the UNLOCK button powers the barcode scanner in the body-worn monitor; this scans a barcode printed on a badge of the nurse of doctor, as described above, and prompts the monitor to render the medical professional view screen 126, shown in FIG. 12B.

Figures 15, 15A, 15B:
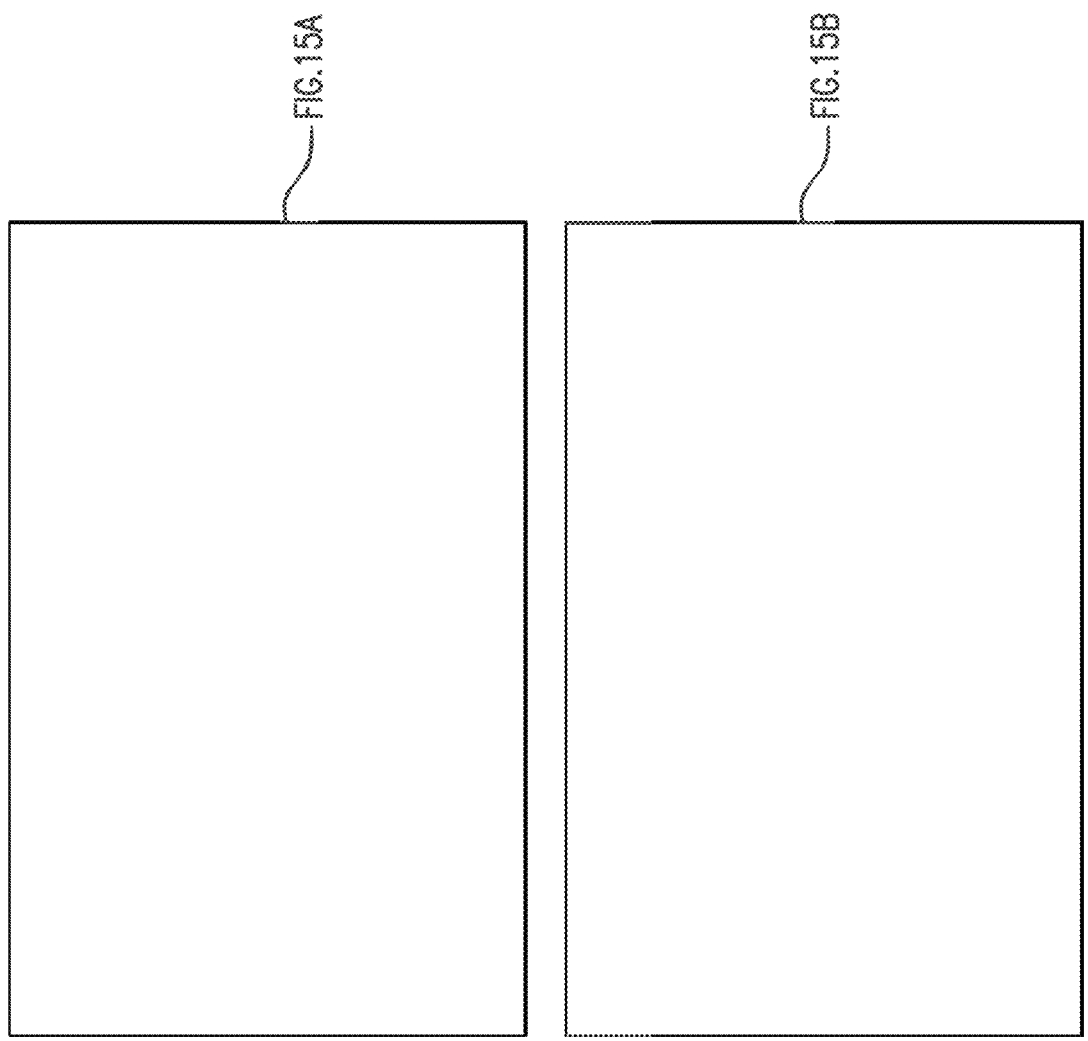
FIG. 15 shows patient and map views used in the GUI rendered on the remote tablet computer of FIG. 14.
FIG. 15A shows a patient view used in the GUI rendered on the remote tablet computer of FIG. 14.
FIG. 15B shows a map view used in the GUI rendered on the remote tablet computer of FIG. 14.
Figure 15B:
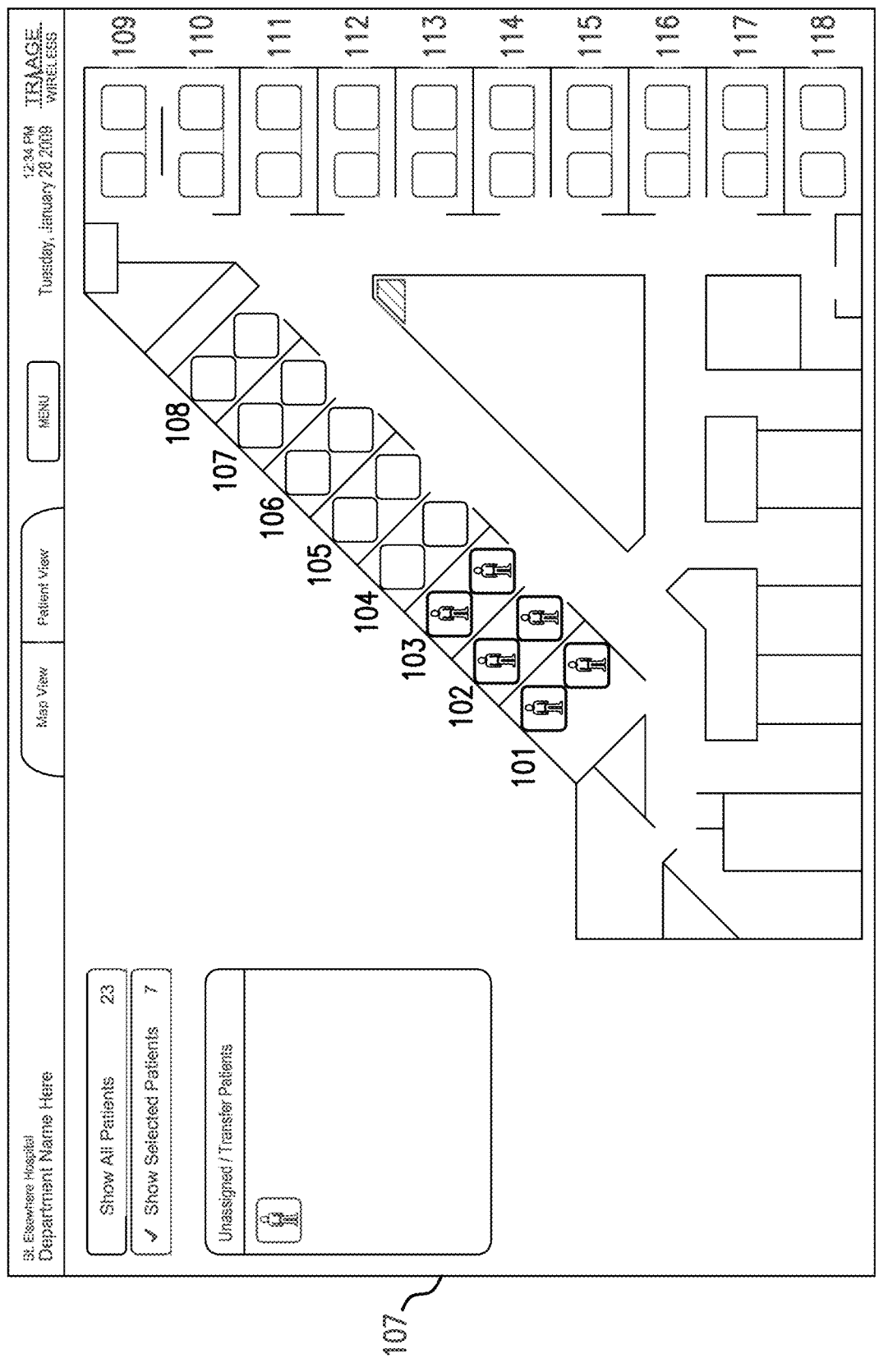

The medical professional view screen 126 is designed to have a 'look and feel' similar to each area 108 of the GUI on the nursing station computer, as shown in FIG. 15A. This makes it relatively easy for the nurse to interpret information rendered on both the body-worn monitor and remote monitor. The screen 126 features fields for a patient identifier, numerical values for vital signs, a time-dependent ECG waveform with a span of approximately 5 seconds, and icons indicating battery life, wireless signal strength, and whether or not an alarm has been generated. A fixed bar proximal to the ECG waveform indicates a signal strength of 1 mV, as required by the AAMI:ANSI EC13 specification for cardiac monitors.

Figure 13:
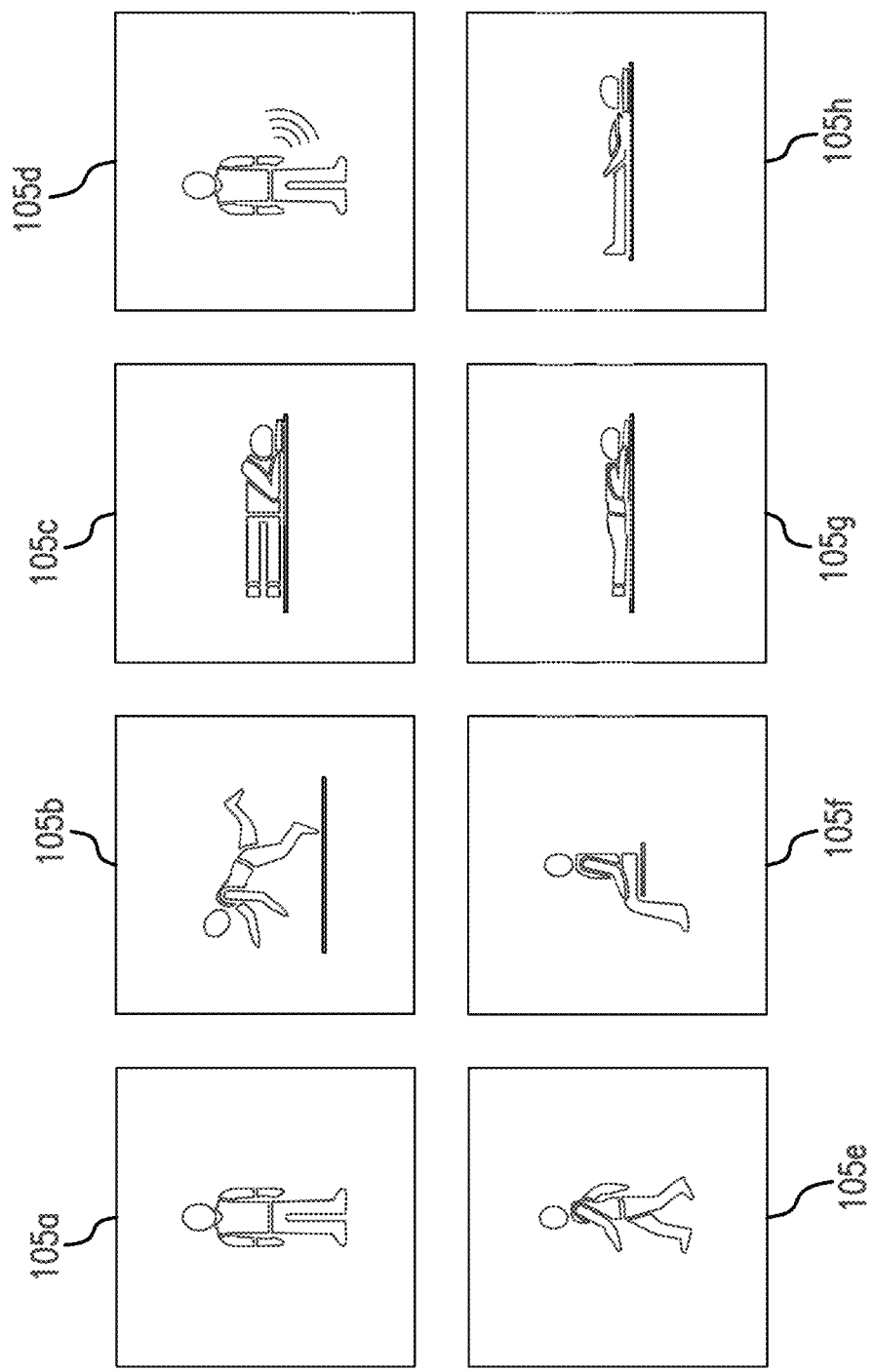
FIG. 13 shows a series of icons used to indicate the patient's posture and activity level in the GUI shown in FIGS. 12C, 15A, and 15B.

The GUI operating on both the body-worn module and the remote monitor can render graphical icons that clearly identify patient activity states, determined as described above from the ACC waveforms. FIG. 13 shows examples of such icons 105a-h, and Table 1, below, describes how they correspond to specific patient activity states. As shown in FIGS. 12A-C and 15A, these icons are used in GUIs for both the body-worn monitor and remote monitor.

TABLE 1 description of icons shown in FIG. 13 and used in GUIs for both body-worn monitor and remote monitor

| Icon | Activity State |
| --- | --- |
| 105a | Standing |
| 105b | Falling |
| 105c | Resting; lying on side |
| 105d | Convulsing |
| 105e | Walking |
| 105f | Sitting |
| 105g | Resting; lying on stomach |
| 105h | Resting; lying on back |

Figure 14:
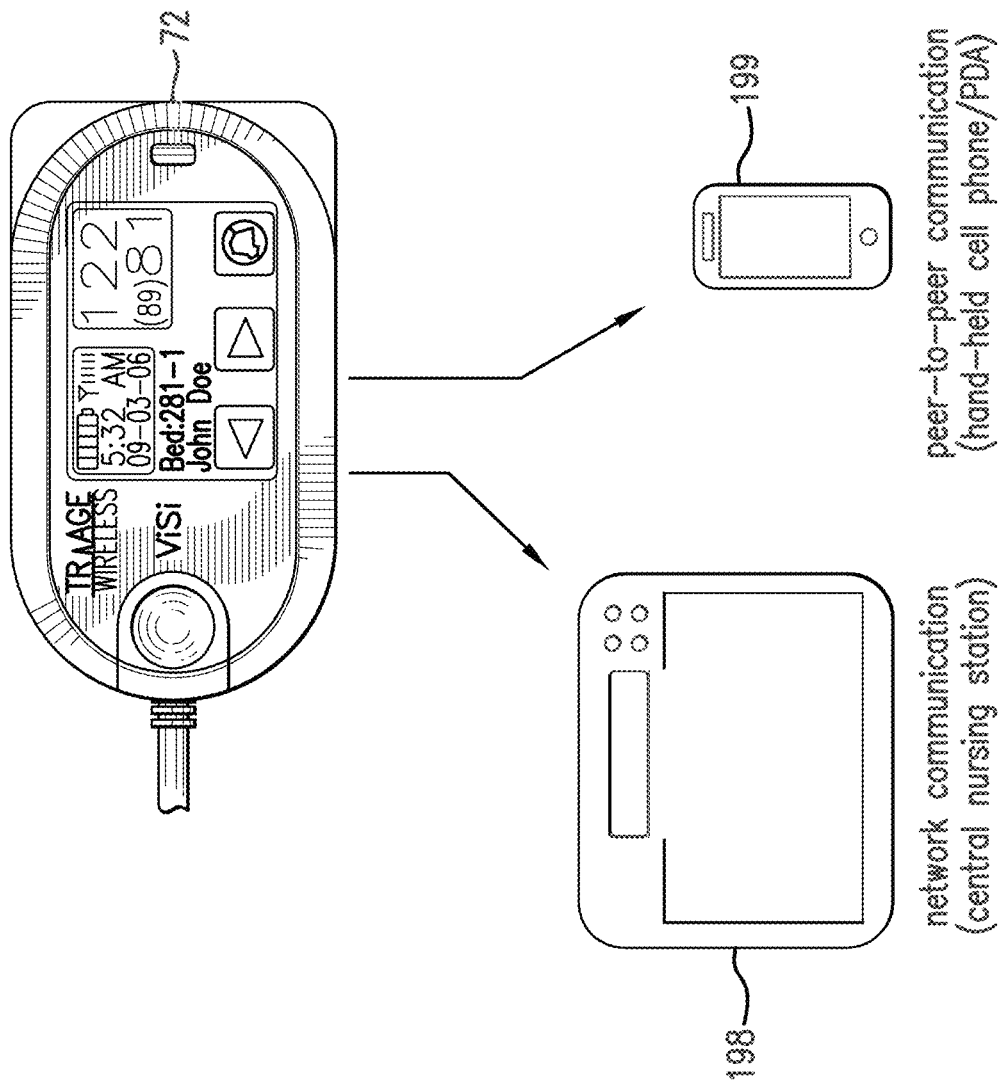
FIG. 14 shows a three-dimensional view of the wrist-worn transceiver of FIG. 5C interfacing with a tablet computer and personal digital assistant (PDA) through, respectively, network and peer-to-peer wireless communication protocols.

FIG. 14 indicates how the wrist-worn transceiver 72 can communicate wirelessly with either a networked computer 198 (e.g. a tablet computer located at a central nursing station) or a hand-held computer 199 (e.g. a cell phone or PDA, typically carried by the medical professional). The specific form of the communication can be determined either manually or automatically. For example, in a normal mode of operation the patient wears the transceiver in their hospital room, and it wirelessly transmits information as described above though a wireless network to the computer 198. Typically this is a network based on 802.11, which is commonplace in the hospital. In a normal mode of operation the computer is associated with a group of patients in an area of the hospital (e.g. a bay of hospital beds, or an ED), and the computer 198 renders a GUI that shows summary information relating to vital signs, motion-related parameters, and alarms/alerts for each patient in the area. A medical professional can 'drill down' on a particular patient by clicking on the portion of the GUI that displays their information.

In another mode of operation, the medical professional can carry the computer 198 into the patient's hospital room for a consultation. In this case, software running on the computer 198 can detect a relatively strong wireless signal strength (RSSI value) associated with the proximal patient, and render their information with the GUI. Alternatively, as described above, the medical professional can manually select this information.

Most portable cellular phones and PDAs have built-in wireless capabilities based on 802.11 and 802.15.4, and thus the wrist-worn transceiver 72 can wirelessly communicate with these devices with a peer-to-peer communication protocol. Typically, in this case, the portable device 199 includes a software application that has been downloaded into its memory, typically from a web-based server. To monitor a particular patient, the medical professional uses the software application to select a particular patient. This process 'pairs' the portable device with the patient's wrist-worn transceiver 72. Once paired, the transceiver sends information for the particular patient to the portable device 199, which then displays it for the medical professional. In other embodiments, the portable device can communicate with the hospital network so that the medical professional can view information for a particular patient even if they are in a different area of the hospital. In still other embodiments, the hospital network is accessible through a cellular network associated with the portable device, and the medial professional can select and view information for a particular patient from any remote location, provided it has good coverage in the cellular network.

FIGS. 15A and 15B show patient (106 in FIG. 15A) and map (107 in FIG. 15B) views from a GUI typically rendered on a remote monitor 198, such as that described above. For example, the different views 106, 107 are generated when a medical professional clicks icons on a GUI rendered by the remote monitor 198 that correspond, respectively, to vital signs 197 and location 196. To generate the GUI the remote monitor 198 simultaneously communicates with multiple body-worn monitors, each deployed on a patient in an area of the hospital. The patient view 106 is designed to give a medical professional, such as a nurse or doctor, a quick, easy-to-understand status of all the patients of all the patients in the specific hospital area. In a single glance the medical professional can determine their patients' vital signs, measured continuously by the body-worn monitor, along with their activity state and alarm status. The view 106 features a separate area 108 corresponding to each patient. Each area 108 includes text fields describing the name of the patient and supervising clinician; numbers associated with the patient's bed, room, and body-worn monitor; and the type of alarm generated from the patient. As described above, this area 108 has a similar 'look and feel' to the interface rendered on the wrist-worn transceiver. Graphical icons, similar to those shown in FIG. 14, indicate the patient's activity level. Additional icons show the body-worn monitor's battery power, wireless signal strength, and whether or not an alarm has been generated. Each area 108 also clearly indicates numerical values for each vital sign measured continuously by the body-worn monitor. The monitor displaying the patient view 106 typically includes a touchpanel. Tapping on the patient-specific area 108 generates a new view (not shown in the figure) that expands all the information in the area 108, and additionally shows time-dependent ECG and PPG waveforms corresponding to the patient.

FIG. 15B shows a map view 107 that indicates the location and activity state of each patient in the hospital area. Each patient's location is typically determined by processing the wireless signal from their body-worn monitor (e.g., by triangulating on signals received by neighboring 802.11 base stations, or simply using proximity to the base station) or by using more advanced methods (e.g. time-of-flight analysis of the wireless signal, or conventional or network-assisted GPS), both of which are done using techniques known in the art. The patient's location is mapped to a grid representing the distribution of beds in the hospital area to generate the map view 107. The map view 107 typically refreshes every 10-20 seconds, showing an updated location and activity state for each patient.

Continuous Patient Monitoring in the Hospital

Figure 16:
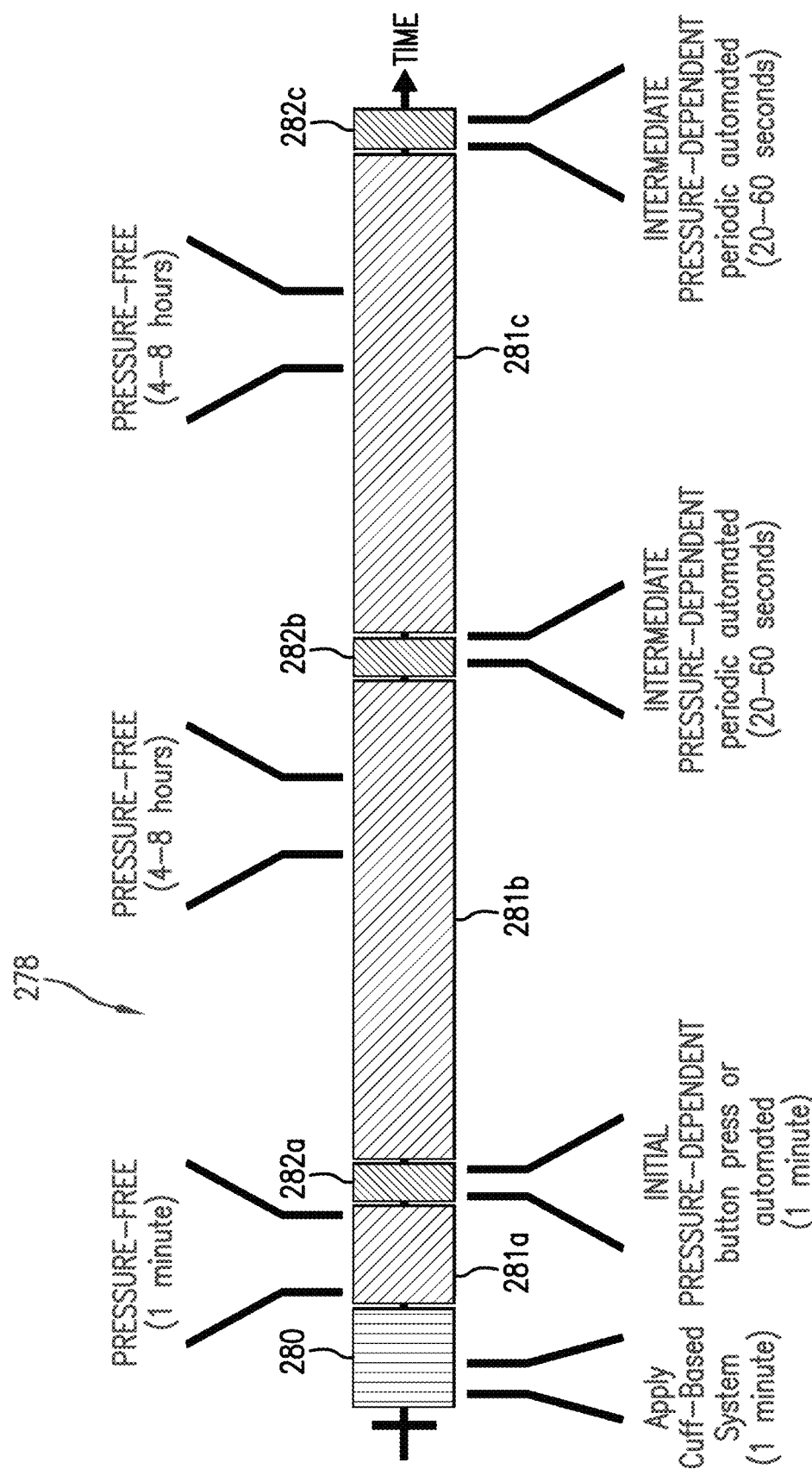
FIG. 16 is a schematic drawing showing a sequence of pressure-dependent and pressure-free measurements made according to the Composite Technique using the body-worn monitor of FIGS. 4A and 4B.

FIG. 16 shows one possible sequence 278 of how the body-worn monitor described above can characterize a hospitalized patient using the Composite Technique, which includes an initial pressure-dependent (step 282*a*), pressure-free (steps 281*a*, 281*b*, 281*c*), and intermediate pressure-dependent (steps 282*b*, 282*c*) measurements for a patient undergoing an extended hospital stay. During the stay, a medical professional applies the body-worn monitor to the patient (step 280). This takes about 1 minute. The medical professional may also collect biometric information from the patient, such as their age, weight, height, gender, ethnicity, and whether they are on blood pressure medications, and enter these into the monitor using a GUI and touchpanel, as described above. This information is then communicated wirelessly through the hospital network. Going forward, the CPU within the wrist-worn transceiver first initiates a pressure-free measurement (step 281*a*) for about 1 minute, wherein the body-worn monitor collects PPG and ECG waveforms from the patient to determine their heart rate and PTT values. In the absence of an absolute blood pressure measurement from the Composite Technique's pressure-dependent measurement, the microprocessor may use PTT and the patient's biometric information to estimate blood pressure, as is described in the following patent application, the contents of which are fully incorporated herein by reference: 1) DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); and 2) VITAL SIGN MONITOR FOR CUFFLESSLY MEASURING BLOOD PRESSURE CORRECTED FOR VASCULAR INDEX (U.S. Ser. No. 12/138,199; filed Jun. 12, 2008). This process typically determines systolic and diastolic blood pressure with an accuracy of about ±10-15 mmHg.

The initial, approximate value for the patient's blood pressure and heart rate determined during the first pressure-free measurement (step 281*a*) can then be used to set certain parameters during the following first pressure-dependent measurement (step 282*a*). Knowledge of these parameters may ultimately increase the accuracy of the initial pressure-dependent measurement (step 282*a*). Such parameters, for example, may include inflation time and rate, fitting parameters for determining the time-dependent increase in PTT and the time-dependent decrease in PPG waveform amplitude during the pressure-dependent measurement. Of particular importance is an accurate value of the patient's heart rate determined during the first pressure-free measurement (step 281*a*). Since both PTT and amplitude can only be measured from a pulse induced by a heartbeat, the algorithm can process heart rate and use it in the fitting process to accurately determine the pressure at which the PPG waveform amplitude crosses zero.

Using parameters such as heart rate and initial estimated blood pressure, the first pressure-dependent measurement (step 282*a*) determines a relationship between PTT and blood pressure as described above. This takes about 60 seconds. This measurement may occur automatically (e.g., after about 1 minute), or may be driven by the medical professional (e.g., through a button press). The microprocessor then uses this relationship and a measured value of PTT to determine blood pressure during the following pressure-free measurement (step 281*b*). This measurement step typically proceeds for a well-defined period of time (typically 4-8 hours), during which it continuously determines blood pressure. Typically, the body sensor averages PTT values over a 10-20 second period, and displays a new blood pressure measurement every second using a rolling average.

The microprocessor may also perform a pre-programmed or automated intermediate pressure-dependent measurement (step 282*b*) to correct any drift in the blood pressure measurement. This measurement is similar to the initial pressure-dependent measurement 282*a*. At some later time, if the patient experiences a sudden change in other vital signs (e.g., respiratory rate, heart rate, body temperature), the CPU in the wrist-worn transceiver may analyze this condition and initiate another pressure-dependent blood pressure measurement (step 282*c*) to most accurately determine the patient's blood pressure.

In addition to those methods described above, a number of additional methods can be used to calculate blood pressure from the PPG and ECG waveforms. These are described in the following patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) CUFFLESS BLOOD PRESSURE MONITOR AND ACCOMPANYING WIRELESS MOBILE DEVICE (U.S. Ser. No. 10/967,511; filed Oct. 18, 2004); 5) BLOOD PRESSURE MONITORING DEVICE FEATURING A CALIBRATION-BASED ANALYSIS (U.S. Ser. No. 10/967,610; filed Oct. 18, 2004); 6) PERSONAL COMPUTER-BASED VITAL SIGN MONITOR (U.S. Ser. No. 10/906,342; filed Feb. 15, 2005); 7) PATCH SENSOR FOR MEASURING BLOOD PRESSURE WITHOUT A CUFF (U.S. Ser. No. 10/906,315; filed Feb. 14, 2005); 8) PATCH SENSOR FOR MEASURING VITAL SIGNS (U.S. Ser. No. 11/160,957; filed Jul. 18, 2005); 9) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 10) HAND-HELD MONITOR FOR MEASURING VITAL SIGNS (U.S. Ser. No. 11/162,742; filed Sep. 21, 2005); 11) CHEST STRP FOR MEASURING VITAL SIGNS (U.S. Ser. No. 11/306,243; filed Dec. 20, 2005); 12) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 13) BILATERAL DEVICE, SYSTEM AND METHOD FOR MONITORING VITAL SIGNS (U.S. Ser. No. 11/420,281; filed May 25, 2006); 14) SYSTEM FOR MEASURING VITAL SIGNS USING BILATERAL PULSE TRANSIT TIME (U.S. Ser. No. 11/420,652; filed May 26, 2006); 15) BLOOD PRESSURE MONITOR (U.S. Ser. No. 11/530,076; filed Sep. 8, 2006); 16) TWO-PART PATCH SENSOR FOR MONITORING VITAL SIGNS (U.S. Ser. No. 11/558,538; filed Nov. 10, 2006); and, 17) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing units and probes for measuring SpO2 similar to those described above can be modified and worn on other portions of the patient's body. For example, probes with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's best). In still other embodiments the probe and processing unit are integrated into a single unit.

Still other embodiments are within the scope of the following claims.

The invention claimed is:

1. A system for measuring vital signs and motion from a patient, comprising:
   (a) a first module comprising a housing configured to be worn on the chest of the patient and an electrocardiogram (ECG) circuit and a three axis accelerometer contained within the housing, wherein (i) the ECG circuit is in electrical communication with at least three ECG leads and generates therefrom a time-dependent digital ECG waveform for each of the ECG leads and transmits the resulting time-dependent digital ECG waveforms as network packets comprising a header portion that indicates the origin of the packet, and a data portion, and (ii) the three axis accelerometer generates a time-dependent digital motion waveform for each of the three axes and transmits the resulting time-dependent digital motion waveforms as network packets comprising a header portion that indicates the origin of the packet, and a data portion; and
   (b) a processing component comprising a housing configured to be worn on the patient's lower arm and a microprocessor and a serial transceiver within the housing and a display on a surface of the housing, wherein the processing component is configured to communicate with the first module to receive the network packets containing the time-dependent digital ECG waveforms and the network packets containing the time-dependent digital motion waveforms;
   wherein the processing component communicates with the first module to transmit a timing synchronizing packet that is received and used by the first module to time-synchronize the network packets containing the time-dependent digital ECG waveforms and the network packets containing the time-dependent digital motion waveforms for processing by the processing component such that there is a maximum 40-microsecond timing error in the synchrony between the time-dependent digital ECG waveforms and the time-dependent digital motion waveforms, and
   wherein the processing component is configured to display the time-dependent digital ECG waveforms and a motion state determined using the time-dependent digital motion waveforms on the processing component display.

* * * * *